(12) United States Patent
Gallagher

(10) Patent No.: US 10,695,143 B2
(45) Date of Patent: Jun. 30, 2020

(54) MEDICAL DEVICE PACKAGE

(71) Applicant: Medtronic Vascular Inc., Santa Rosa, CA (US)

(72) Inventor: John Gallagher, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 15/897,457

(22) Filed: Feb. 15, 2018

(65) Prior Publication Data

US 2019/0247137 A1 Aug. 15, 2019

(51) Int. Cl.
*B65D 83/10* (2006.01)
*A61B 50/33* (2016.01)
(Continued)

(52) U.S. Cl.
CPC ............ *A61B 50/33* (2016.02); *A61B 50/30* (2016.02); *A61L 2/26* (2013.01); *B65B 5/04* (2013.01); *B65B 7/2878* (2013.01); *B65B 15/00* (2013.01); *B65D 77/04* (2013.01); *B65D 77/2024* (2013.01); *B65D 77/28* (2013.01); *A61B 50/20* (2016.02); *A61B 2050/005* (2016.02); *A61B 2050/0056* (2016.02);
(Continued)

(58) Field of Classification Search
CPC ............ A61B 50/33; A61B 2050/005; A61B 2050/3015; A61B 2050/314; A61B 50/31; A61B 2050/311; A61M 25/00; A61M 25/002; B65B 5/04; B65B 7/28; B65B 7/2878; B65B 15/00; B65D 73/00; B65D 73/0014; B65D 77/20; B65D 77/2024; B65D 77/28; B65D 85/00; B65D 85/20; B65D 85/24

USPC .................. 206/363-370, 477-483; 604/228
See application file for complete search history.

(56) References Cited

U.S. PATENT DOCUMENTS

| 5,127,518 | A | * | 7/1992 | Holzwarth | ....... | A61B 17/06138 206/63.3 |
| 5,199,561 | A | * | 4/1993 | Roshdy | ............ | A61B 17/06138 206/227 |

(Continued)

FOREIGN PATENT DOCUMENTS

EP 3100697 A1 12/2016

OTHER PUBLICATIONS

International Search Report and Written Opinion, PCTUS2019/018059, dated Jun. 5, 2019.

*Primary Examiner* — Luan K Bui
(74) *Attorney, Agent, or Firm* — Medler Ferro Woodhouse & Mills PLLC

(57) ABSTRACT

In some examples, a medical device package may include a backing card that is configured to secure a medical device to a major surface of the backing card. The backing card is configured to be assembled from an open state into a closed state in which flaps on one or more ends of a central region of the backing card move over some of the central region and cover some of the secured medical device. The closed state defines a reduced footprint relative to the unfolded state. The backing card may be sealed in a pouch, which may then be housed in a carton. The carton includes exterior walls that enclose the sealed backing card and spacing elements that receive the sealed backing card at a relative location within the carton and holds the backing card a threshold distance from the exterior walls of the carton.

14 Claims, 14 Drawing Sheets

(51) Int. Cl.
    *B65D 77/20*       (2006.01)
    *B65D 77/28*       (2006.01)
    *B65B 5/04*        (2006.01)
    *B65B 15/00*       (2006.01)
    *B65B 7/28*        (2006.01)
    *A61B 50/30*       (2016.01)
    *B65D 77/04*       (2006.01)
    *A61L 2/26*        (2006.01)
    *A61B 50/00*       (2016.01)
    *A61B 50/20*       (2016.01)

(52) U.S. Cl.
    CPC ............... *A61B 2050/0058* (2016.02); *A61B 2050/3008* (2016.02); *A61B 2050/3015* (2016.02); *A61B 2050/314* (2016.02); *A61L 2202/181* (2013.01); *A61L 2202/24* (2013.01)

(56) References Cited

U.S. PATENT DOCUMENTS

| | | | | |
|---|---|---|---|---|
| 5,234,106 A * | 8/1993 | Transue | ............... | A61B 50/30 206/363 |
| 5,351,822 A * | 10/1994 | Sinn | ............... | B65D 73/0021 206/363 |
| 5,375,717 A * | 12/1994 | Roshdy | ............... | B65D 73/0021 206/363 |
| 5,425,445 A * | 6/1995 | Brown | ............... | A61B 17/06138 206/380 |
| 5,487,469 A * | 1/1996 | Roshdy | ............... | A61B 17/06138 206/363 |
| 5,501,341 A * | 3/1996 | Van Es | ............... | A61M 25/002 206/364 |
| 5,529,175 A * | 6/1996 | Brunken | ............... | A61B 17/06138 206/63.3 |
| 5,533,611 A * | 7/1996 | Bordighon | ............... | A61B 17/06138 206/227 |
| 5,566,821 A * | 10/1996 | Brown | ............... | A61B 17/06138 206/388 |
| 5,788,063 A * | 8/1998 | Van Ness | ............... | A61B 17/06138 206/380 |
| 6,068,121 A | 5/2000 | McGlinch | | |
| 6,892,881 B2 * | 5/2005 | Leitch | ............... | A61M 25/002 206/364 |
| 7,328,794 B2 * | 2/2008 | Lubs | ............... | A61M 25/002 206/364 |
| 8,113,348 B2 * | 2/2012 | Foster | ............... | A61M 25/002 206/363 |
| 9,498,317 B2 | 11/2016 | Gautam et al. | | |
| 9,522,251 B2 * | 12/2016 | Katsuno | ............... | B65D 73/0014 |
| 9,776,783 B2 * | 10/2017 | Nadig | ............... | B65D 77/04 |
| 2005/0211595 A1 * | 9/2005 | Hull | ............... | B65D 5/509 206/523 |
| 2005/0278012 A1 | 12/2005 | Vonderwalde | | |
| 2012/0310332 A1 | 12/2012 | Murray et al. | | |
| 2017/0056149 A1 | 3/2017 | Rajpara et al. | | |
| 2018/0071043 A1 | 3/2018 | Dacey et al. | | |

\* cited by examiner

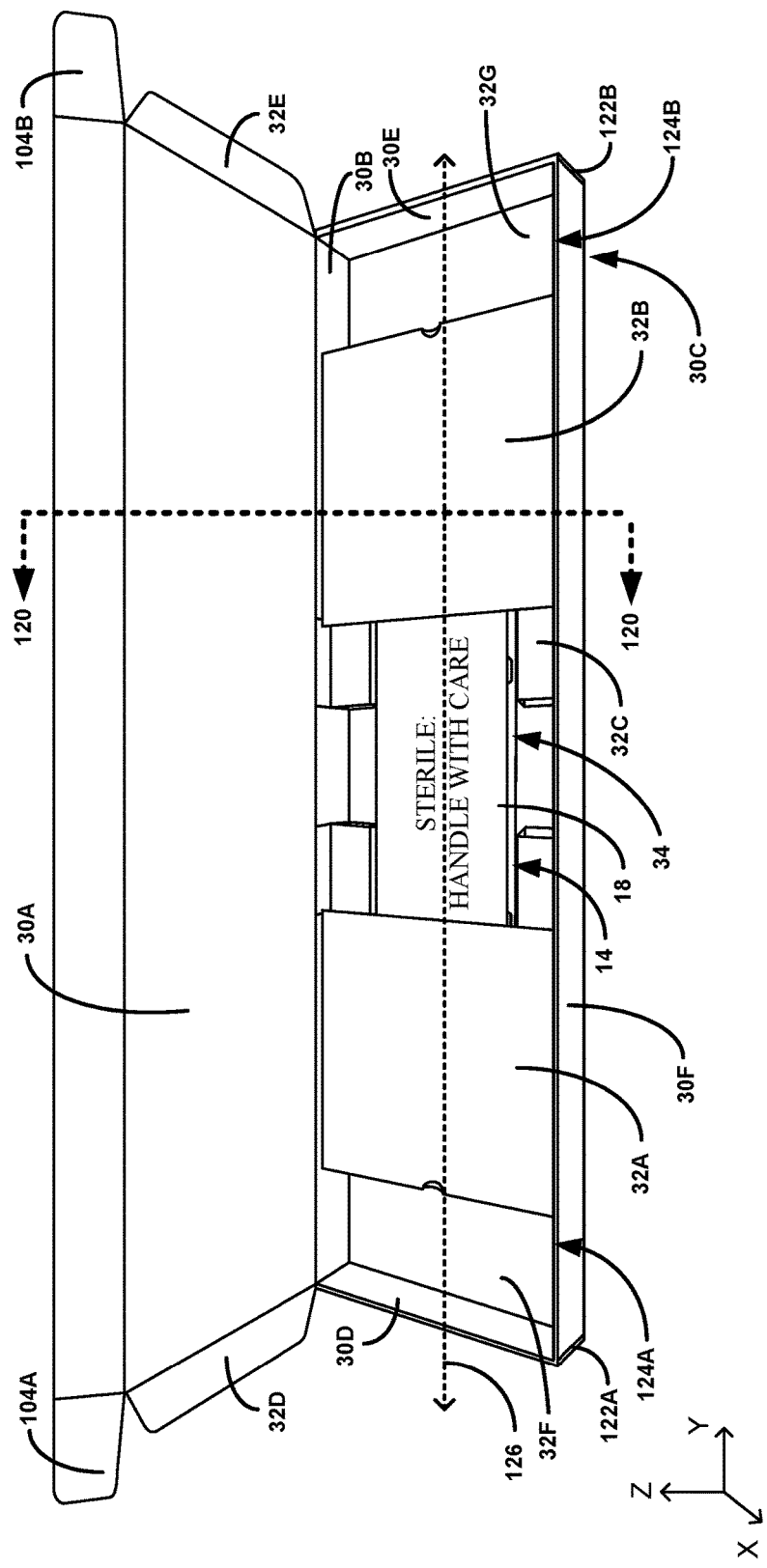
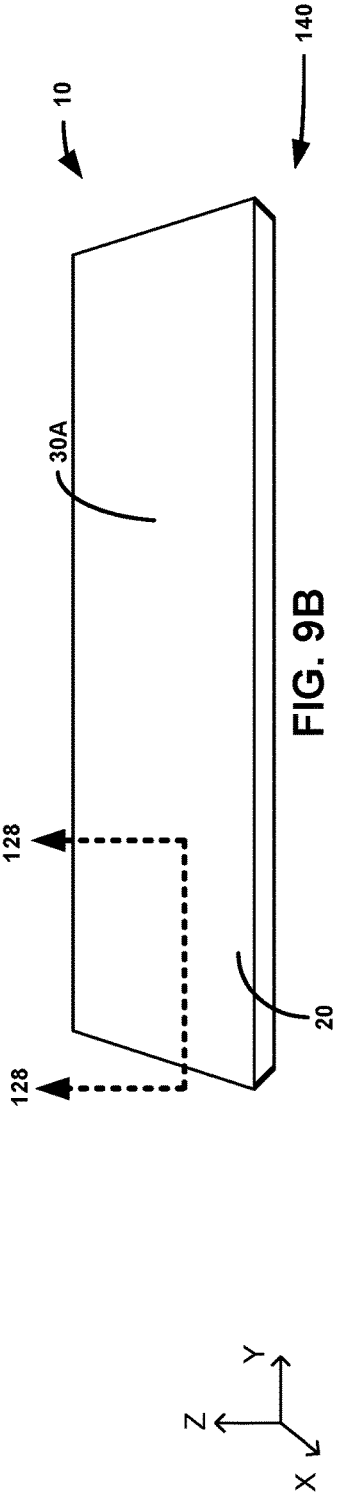
FIG. 9A
FIG. 9B

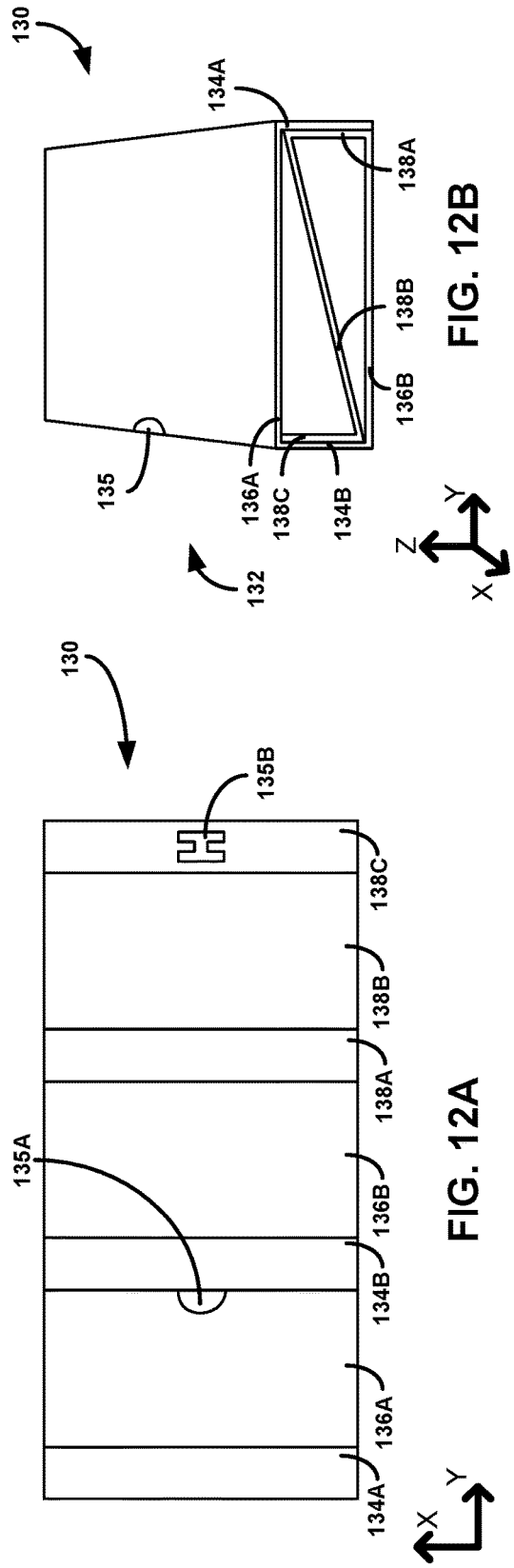
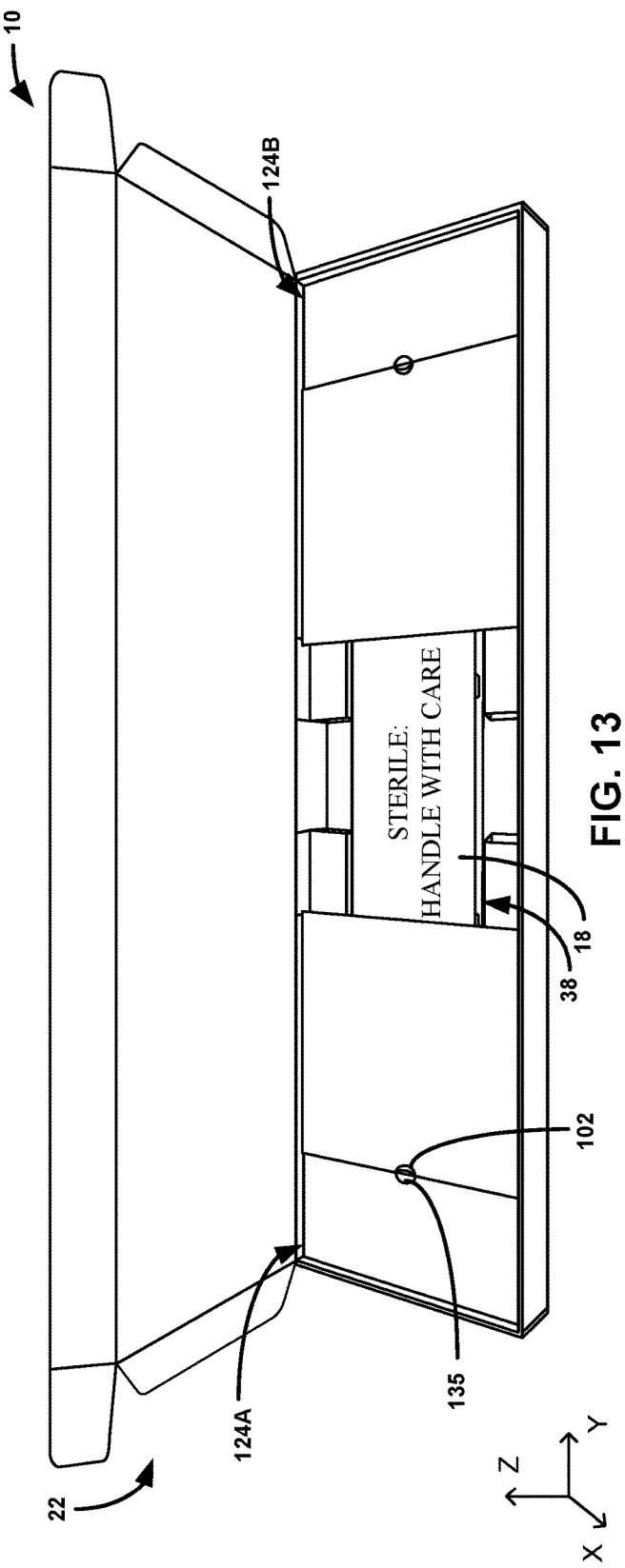

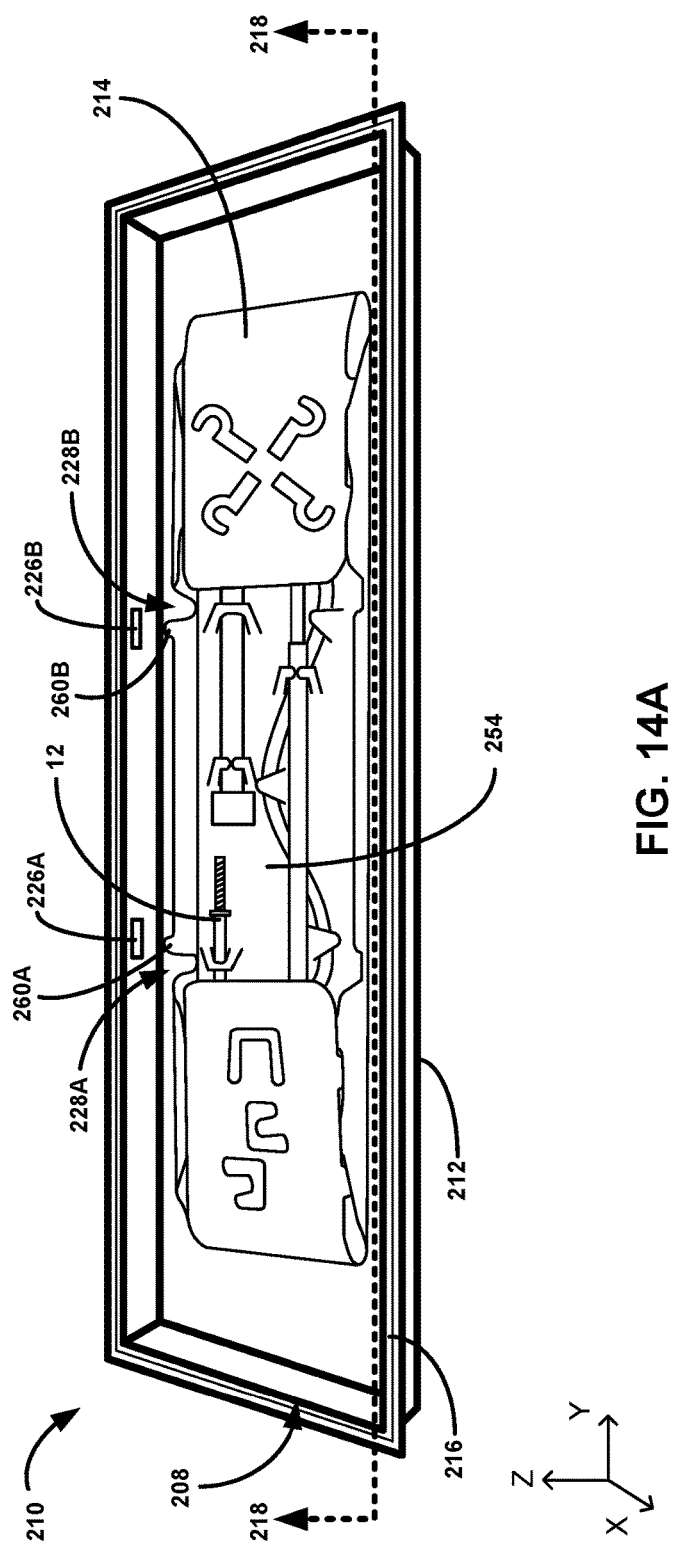
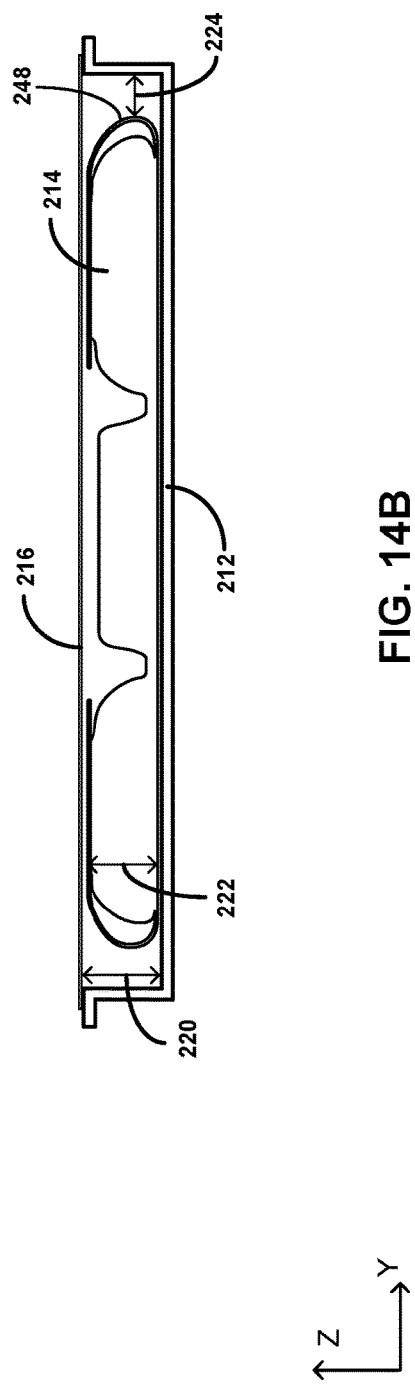
FIG. 14A
FIG. 14B

MEDICAL DEVICE PACKAGE

TECHNICAL FIELD

This disclosure relates to packages for medical devices.

BACKGROUND

Medical devices may be hermetically sealed in bags or pouches prior to use. Further, the bags or pouches sealing the medical devices may themselves be packaged in a relatively compact configuration prior to use. For example, sealed medical devices may be packaged in boxes that enclose the sealed bags or pouches.

SUMMARY

This disclosure describes example medical device packages that are configured to receive and house medical devices. An example medical device package described herein includes a backing card that is configured to secure a medical device to a major surface of the backing card. The backing card is configured to be assembled from an unfolded state into a closed state, in which flaps on one or more ends of a central region of the backing card move over or "cover" some of the central region and cover at least a portion of a medical device that is secured to the major surface of the backing card. In the closed state, the backing card has a reduced footprint relative to when it is in the unfolded state. Once in the closed state, the backing card may be sealed in a pouch, which may then be housed in a carton. The carton may have exterior walls that enclose the sealed backing card. Further, the carton may include spacing elements that receive the sealed backing card at a relative location within the carton and holds the backing card a threshold distance from the exterior walls of the carton.

In one example, a medical device package includes a backing card defining a longitudinal axis, the backing card including: a major surface configured to receive a medical device when the backing card is in an open state, the major surface extending lengthwise along the longitudinal axis of the backing card and including a central region and one or more flaps at one or more ends of the major surface, wherein the central region is between two longitudinal ends of the major surface; and a plurality of tabs configured to extend away from the major surface to secure the medical device to the major surface, wherein at least a portion of each of the flaps is configured to move over at least a portion of the central region along the longitudinal axis to assemble the backing card into a closed state that at least partially encloses the secured medical device.

In some examples of the medical device package of the above example, the central region and the one or more flaps define a substantially flat plane in the open state.

In some examples of the medical device package of any of the examples above, the medical device is configured to be secured to both the central region and the one or more flaps of the major surface.

In some examples of the medical device package of any of the examples above, at least some tabs of the plurality of tabs are configured to extend in a direction transverse to the major surface.

In some examples of the medical device package of any of the examples above, the central region is configured to removably couple to each of the one or more flaps when the backing card is in the closed state to secure the backing card in the closed state.

In some examples of the medical device package of any of the examples above, the one or more flaps are substantially parallel with the central region when the backing card is in the closed state.

In some examples of the medical device package of any of the examples above, the medical device package further includes a carton configured to receive the backing card when the backing card is in the closed state, the carton including: a set of exterior walls configured to completely enclose the backing card in the closed state when the carton is in a storage state; and a plurality of spacing elements attached to the exterior walls, the spacing elements being configured to receive the backing card in the closed state when the carton is in a receiving state, the plurality of spacing elements configured to secure the backing card at a position with at least a threshold distance between an outer surface of the backing card and the nearest respective portion of the exterior walls when the set of exterior walls encloses the backing card when the carton is in the storage state.

In some examples of the medical device package of the example above including the carton, the set of exterior walls of the carton defines an orthotope when the carton is in the storage state.

In some examples of the medical device package of any of the examples above including the carton, the backing card is a first backing card, wherein at least some of the spacing elements are adjustable to secure both the first backing card and a second backing card with at least the threshold distance between an outer surface of the respective backing card and the nearest respective portion of the exterior walls, wherein the first backing card is a different size than the second backing card.

In some examples of the medical device package of any of the examples above including the carton, the backing card is physically accessible along an axis that is perpendicular to the longitudinal axis of the backing card when the plurality of spacing elements has received the backing card and the carton is in the receiving state.

In some examples of the medical device package of any of the examples above including the carton, the plurality of spacing elements is configured to engage the backing card along a length of the longitudinal axis of the backing card when the carton is in the storage state, such that the plurality of spacing elements apply a stabilizing force to the backing card in response to a motion of the backing card in the carton relative to the carton, where the stabilizing force is opposed to the motion.

In some examples of the medical device package of the example above, the carton defines two gaps at longitudinal ends of the carton between a longitudinal exterior wall of the set of exterior walls and a nearest respective spacing element of the plurality of spacing elements when the backing card is received by the plurality of spacing elements and the carton is in the receiving state, wherein a top exterior wall of the set of exterior walls that is configured to close over the backing card to move the carton into the closed state is attached to spacing elements that are configured to occupy the two gaps and applying the stabilizing force to the backing card.

In some examples of the medical device package of any of the examples above, the medical device package further includes a pouch configured to enclose the backing card, the pouch configured to create a hermetic seal around the backing card.

In some examples of the medical device package of any of the examples above, the medical device package further includes a tray defining a recess configured to receive the backing card, the tray including a layer configured to hermetically seal the recess when the recess receives the backing card.

In some examples of the medical device package of any of the examples above, the one or more flaps are configured to bend over at least the portion of the central region along the longitudinal axis without creating a crease in the major surface.

In some examples of the medical device package of any of the examples above, each tab of a subset of the plurality of tabs includes a relatively straight section that extends away from the major surface and terminates in a hook shape, wherein the subset of tabs is arranged around a central point on the major surface and is configured to extend away from the major surface and secure a medical component centered on the central point using the hook shapes.

In some examples of the medical device package of any of the examples above, the backing card is configured to secure a portion of the medical device on the central region of the major surface, wherein the backing card is configured to expose the portion of the medical device when the backing card is in the closed state.

In some examples of the medical device package of any of the examples above, the medical device package further includes the medical device.

In some examples of the medical device package of any of the examples above, the backing card defines a substantially consistent height across the longitudinal axis of the backing card when the backing card is in the closed state, wherein the height is measured along an axis that is substantially perpendicular to the longitudinal axis.

In some examples of the medical device package of any of the examples above, the backing card is configured to substantially define only relatively flat surfaces that intersect to define curvilinear surfaces along an outer perimeter of the backing card when the backing card is in the closed state.

In one example, a medical device package includes a medical device and a backing card defining a longitudinal axis, the backing card including: a major surface configured to receive the medical device when the backing card is in an open state, the major surface extending lengthwise along the longitudinal axis of the backing card and including a central region and one or more flaps on one or more ends of the major surface along the longitudinal axis; a plurality of tabs configured to extend away from the major surface to secure the medical device to the major surface, wherein at least a portion of each of the one or more flaps is configured to move over at least a portion of the central region along the longitudinal axis to assemble the backing card into a closed state that at least partially encloses the secured elongated medical device. The medical device package also includes a pouch configured to enclose the backing card, the pouch configured to create a hermetic seal around the backing card, and a carton configured to receive the backing card when the backing card is in the closed state. The carton includes a set of exterior walls configured to completely enclose the backing card in the closed state and a plurality of spacing elements attached to the set of exterior walls, the spacing elements being configured to secure the backing card at a position with at least a threshold distance between an outer surface of the backing card and the nearest respective portion of the exterior walls when the set of exterior walls enclose the backing card.

In some examples of the medical device package of the example above, the carton defines empty space between a longitudinal end of the backing card in the closed state and a longitudinal end of the carton, the medical device package further comprising a support box that is configured to occupy the empty space and provide a stabilizing force on both the longitudinal end of the backing card and the longitudinal end of the carton.

In some examples of the medical device package of any of the examples above, the backing card further includes one or more handles that extend longitudinally from one or more longitudinal ends of the backing card when the backing card is in the open state.

In one example, a method includes: securing a medical device to a major surface of a backing card using a plurality of tabs of the backing card when the backing card is in an open state, the major surface including a central region and one or more flaps at one or more ends of the major surface, wherein the central region is between two longitudinal ends of the major surface; and moving the backing card from the open state to the closed state by moving at least a portion of each of the one or more flaps over at least a portion of the central region such that the one or more flaps at least partially enclose the secured medical device.

In some examples of the method above, the method further includes sealing the backing card in a pouch after moving the backing card to the closed state.

In some examples of any of the methods above, the method further includes loading the backing card into a channel of a carton that includes a set of exterior walls and a plurality of spacing elements attached to the set of exterior walls, the plurality of spacing elements defining the channel at a position with at least a threshold distance between an outer surface of the backing card and the nearest respective portion of the set of exterior walls.

In some examples of any of the methods above, the method further includes moving the carton into a storage state in which the set of exterior walls completely enclose the backing card as received at the location in the channel.

In some examples of any of the methods above, the method further includes adjusting one or more spacing elements of the carton to modify the threshold distance.

In some examples of any of the methods above, the method further includes loading the backing card into a recess of a tray and placing a film over a mouth of the recess to hermetically seal the backing card into the recess of the tray, wherein the tray defines substantially no unobstructed space between outer surfaces of the backing card and inner surfaces of tray when the backing card is loaded into the tray.

In some examples of any of the methods above, the backing card is part of a medical device package of any of the examples above.

The details of one or more examples are set forth in the accompanying drawings and the description below. Other features, objects, and advantages will be apparent from the description and drawings, and from the claims.

BRIEF DESCRIPTION OF DRAWINGS

FIG. 9A is a conceptual and schematic diagram illustrating a perspective view of the identification card, the backing card, and the pouch of FIG. 1A positioned within the carton of FIG. 1A.

FIG. 9B is a conceptual and schematic diagram illustrating a perspective view of the medical device package of FIG. 1A when the carton is in the storage state.

FIGS. 12A and 12B are conceptual and schematic diagrams illustrating a plan and perspective view, respectively, of a box support that may be used to help secure the medical device within the medical device package of FIG. 1A.

FIG. 13 is a conceptual and schematic diagram illustrating a perspective view of the identification card, the backing card, and the pouch of FIG. 1A positioned within the carton of FIG. 1A when secured using the box support of FIGS. 12A and 12B.

FIG. 14A is a conceptual and schematic diagram illustrating a perspective view of another example medical device package, the medical device package including the backing card of FIG. 1A received in a tray and sealed by a film.

FIG. 14B is a conceptual and schematic diagram illustrating a cross-sectional view the medical device package of FIG. 14A taken along line 218-218 of FIG. 14A.

DETAILED DESCRIPTION

Figure 1A:
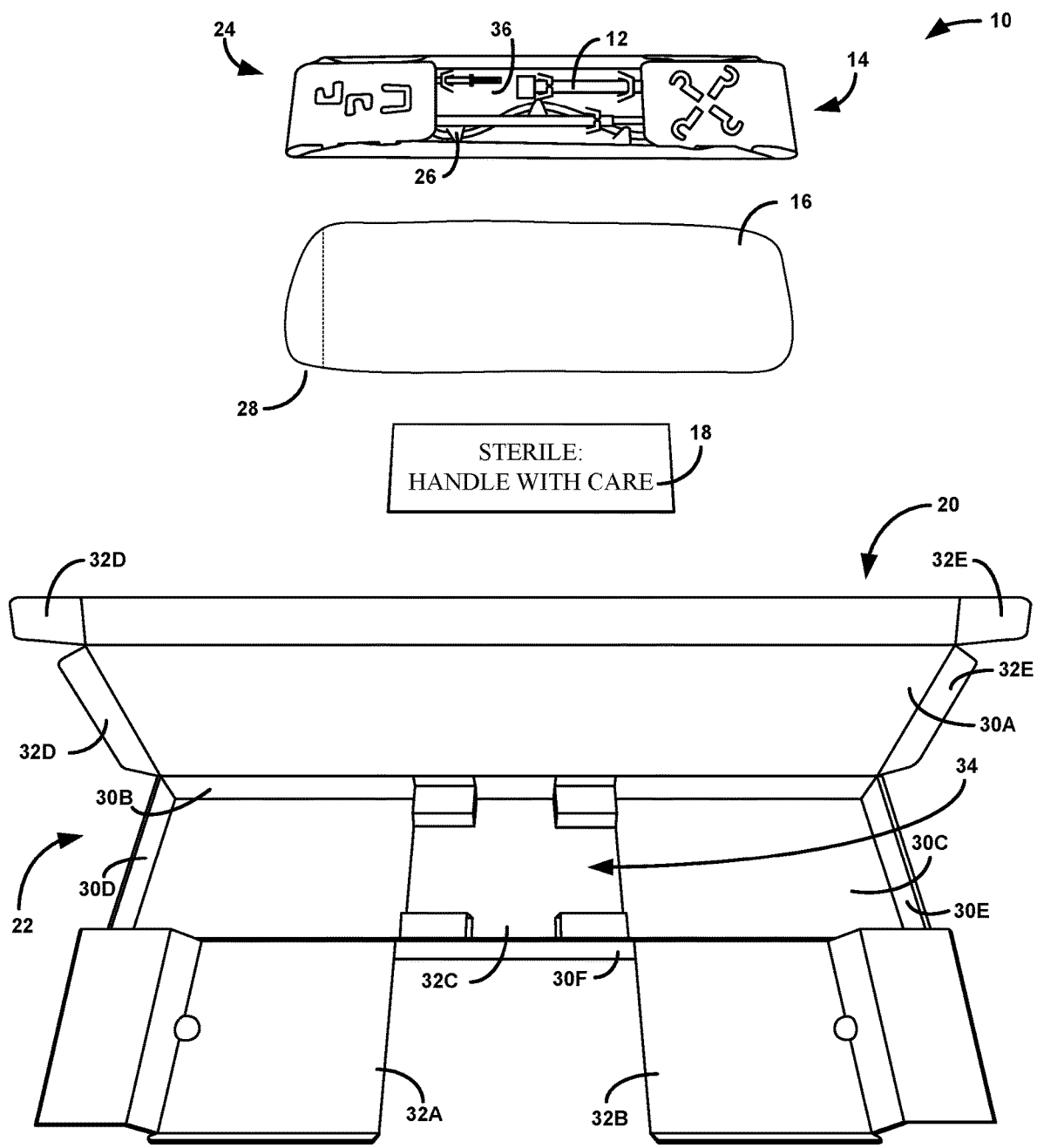
FIG. 1A is a conceptual and schematic diagram illustrating an exploded perspective view of an example medical device package that includes a backing card, a pouch, an identification card, and a carton.

A medical device may be packaged in a medical device package for shipment and storage after manufacture and before being used, e.g., in a medical procedure. The medical device package is configured to create a sterile compartment in which the medical device may be housed during shipment and storage (e.g., by hermetically sealing the medical device within the sterile compartment of the medical device package). In examples described herein, a medical device package includes a backing card. The backing card may define a major surface that includes a central region and one or more flaps at one or more ends of the central region. Accordingly, where there are two or more flaps the central region may be located between the flaps. The major surface is configured to receive the medical device when the backing card is in an open state, in which the major surface (including the central region and the flaps) defines a substantially flat plane when placed (e.g., by a manufacturing user or machine) on a substantially flat surface.

The medical device may be secured to the major surface of the backing card by a plurality of tabs that are configured to extend away from the major surface. In some examples, the medical device is secured to both the central region and the flaps of the backing card. In other examples, the medical device may be secured to only the central region. Once the medical device is secured to the major surface, the backing card may be moved (e.g., one portion of the backing card being curled or deformed into a new position relative to other relatively stationary portions of the backing card) into a closed state by moving the flaps of the backing card to at least partially over the central region, therein partially enclosing the medical device and reducing a footprint of the backing card.

Configuring the backing card such that a medical device can be secured to numerous sections of the backing card, some of which may then be moved to partially overlap other securing sections, may enable the backing card to securely hold the medical device in a relatively reduced footprint, e.g., compared to a backing card that does not have flaps that can extend over a central region. The reduced footprint medical device package enabled by the backing card may provide for more efficient storage of the medical device. Further, securing the medical device to the backing card in this manner configuration may help reduce shipping costs, provide for easier/less awkward manipulation of the medical device package, or any combination thereof.

Once in the closed state, the backing card may be sealed in a pouch and received by a carton or other outer housing. In some examples, the pouch is configured to hermetically package the backing card. The pouch may help isolate the medical device from the surrounding environment and/or help prevent contamination of the medical device during shipping and/or storage. Further, by reducing a footprint of the backing card, the pouch may itself have a reduced footprint relative to a pouch that is configured to enclose a non-foldable backing card for a like-sized medical device. Reducing a footprint of the sealed pouch that contains the backing card in the closed state may reduce or eliminate the likelihood that the pouch may need to be folded or otherwise substantially condensed or stressed when received by the carton or other outer housing. Reducing or eliminating folds or stresses put upon the pouch may reduce the chances that the pouch will tear or otherwise inadvertently open during storage or shipment, thereby improving the integrity of the medical device package.

The carton may include exterior walls configured to completely enclose the backing card, and a plurality of spacing elements that define a space for the backing card and pouch within the exterior walls and space the backing card and pouch from the exterior walls of the carton (e.g., the buffer as described above). The spacing elements may be configured to hold the sealed pouch (in which the backing card and medical device are positioned) within the carton such that there is a threshold distance between an inner surface of the exterior walls and an outer surface of the sealed pouch around an entirety of the sealed pouch. Configuring the carton such that the backing card that secures the medical device is held at least a threshold distance away from the exterior walls of the carton may reduce a likelihood that physical forces applied to the carton (e.g., as a result of dropping the carton or accidentally denting a corner or section of the corner) adversely affects the integrity of the pouch, the backing card, and/or the medical device. In this way, the carton may be configured to help maintain the structural integrity of the medical device stored within the carton, as well as to help maintain the sterility of the stored medical device by maintaining the structural integrity of the pouch in which the medical device is housed.

FIG. 1A is a conceptual and schematic diagram illustrating an exploded perspective view of an example medical device package 10 for an example medical device 12, where medical device package 10 includes an example backing card 14, an example pouch 16, an example identification card 18, and an example carton 20 that is in an example receiving state 22. FIG. 1A depicts orthogonal x-y-z axes which are referenced herein for ease of description. Medical device 12 may be any medical device suitable for packaging using backing card 14. In some examples, medical device 12 is an elongated device or may include an elongated component, such as, but not limited to, a catheter, a guidewire, an implant delivery system (e.g., a stent delivery device), an instrument such as a thrombectomy device located at the end of an elongated member (e.g., a wire, a hypotube, a combination of wire and hypotube), an electrically conductive lead, an optical fiber, a catheter-deliverable heart valve, or another elongated vascular device. An elongated component of medical device 12 may have a length (e.g., as measured along a longitudinal axis) of three or more meters.

Medical device 12 may be intended for use in a medical procedure, and medical device package 10 is configured to house medical device 12 during shipment and storage of medical device 12. In some examples, medical device package 10 is configured to store medical device 12 in a hermetically sealed environment, e.g., defined by pouch 16. Configuring medical device package 10 to hermetically seal medical device 12 (e.g., within pouch 16) may improve an ability of medical device package 10 to promote the sterility of medical device 12.

Medical device 12 may be secured to backing card 14. Backing card 14 may be a component of medical device package 10 that is configured to move between at least two predetermined states that define at least two different footprints as viewed along the Z-axis direction, where moving involves self-referential motion of one portion of backing card 14 relative to another portion of backing card 14. Within one state that defines a relatively greater footprint, referred to herein as an open state, backing card 14 may be configured to receive and secure medical device 12 in a predetermined configuration such that medical device 12 is accessible (e.g., for viewing and removal from backing card 14). Within another state that defines a relatively smaller footprint, referred to herein as a closed state, backing card 14 may be configured to at least partially enclose (e.g., enclose in more than one direction) a secured medical device 12 while defining a substantially predetermined three-dimensional shape that carton 20 is configured to receive.

Backing card 14 may define the predetermined configuration in which medical device 12 is received and secured to enable backing card 14 to move between these states. In this way, backing card 14 may be configured to first receive medical device 12 in a predetermined configuration and then move into a more compact state in a predetermined manner to orient medical device 12 into a predetermined three-dimensional shape that may be reliably received by the sterile compartment defined by medical device package 10. Further, as described herein, by being configured to move into a more compact state in a predetermined manner, backing card 14 may similarly enable pouch 16 to be more compact as it receives backing card 14 and as pouch 16 and backing card 14 are subsequently received by carton 20, potentially reducing the likelihood of pouch 16 being folded within medical device package 10.

In the example shown in FIG. 1A, backing card 14 includes major surface 36 configured to receive medical device 12. Medical device 12 may be secured to major surface 36 when backing card 14 is in an open state (not depicted in FIG. 1A, and depicted in FIG. 2). As discussed in further detail below with respect to FIG. 2, in the open state of backing card 14, major surface 36 of backing card 14 defines a substantially flat plane. Major surface 36 may be substantially the largest (e.g., by area) surface of backing card 14, and may make up a majority of one side of backing card 14. Backing card 14 is configured to be moved (e.g., one portion of backing card 14 is moved relatively to another relatively stationary portion of backing card 14) from the open state in which backing card 14 receives medical device 12 to the depicted closed state 24.

In some examples, backing card 14 may be a single contiguous part made of a unitary piece of material. For example, backing card 14 may be a cut from, detached from, or otherwise formed out of a relatively large sheet of a material (e.g., a sheet that can be used to form scores or hundreds of substantially similar backing cards 14). The sheet, and therefore respective backing cards 14, may have a substantially uniform cross-sectional thickness. Backing card 14 is relatively deformable, such that backing card 14 may be moved between the open state and closed state 24. In addition, backing card 14 may be configured to be relatively stiff (e.g., self-supporting), such that, e.g., when a user picks up backing card 14 while in closed state 24 (e.g., by a clinician that is handling backing card 14), backing card 14 may stay substantially in the depicting closed state 24, rather than bending or otherwise substantially deforming (e.g., bending in half due to gravitational forces when picked up by an end when other sections of backing card 14 are not supported). Backing card 14 is configured (e.g., based on the materials from which it is formed and/or from its physical shape) such that a user may manipulate backing card 14 between the open and closed states with relatively little force.

Backing card 14 may be made of any suitable material or combination of materials. In some examples, backing card 14 is formed from a polymer-based material, such as, but not limited to, high-density polyethylene (HDPE). In some examples, backing card 14 may include a lubricious coating on major surface 36, such as a hydrophilic coating, a polytetrafluoroethylene (PTFE) coating, or a HDPE coating (e.g., where the rest of the backing card 14 is comprised of a material other than HDPE). The lubricious coating may be configured to reduce friction between major surface 36 and a received medical device 12, which may reduce any adverse interactions between medical device 12 and backing card 14. In some cases, it may be desirable to reduce friction between medical device 12 and backing card 14 in order to, for example, help maintain the integrity of a coating or other surface on medical device 12.

In some examples, the lubricious coating or another coating may help facilitate the attachment of medical device 12 to backing card 14 and/or remove medical device 12 from backing card 14. Further, in some examples, a lubricious coating or other type of coating may improve an ability of backing card 14 to move between an open state and closed state 24 without creating/defining creases and/or sharp edges, which may reduce a likelihood of backing card 14 puncturing or otherwise adversely affecting pouch 16 that houses backing card 14.

Backing card 14 includes a plurality of tabs 26 that are configured to secure medical device 12 to major surface 36 of backing card 14. Examples tabs 26A, 26B, 26C are shown in further detail in FIG. 2. In some examples, tabs 26 are portions of backing card 14 that have been partially cut from backing card 14, such that tabs 26 may move freely (e.g., relative to other portions of backing card 14 and/or the plane defined by major surface 36) in one or more dimensions. In other examples, tabs 26 may be separate from the piece of material defining major surface 36 of backing card 14, and mechanically connected to major surface 36. Tabs 26 may take many shapes as discussed herein to secure medical device 12. In some examples, backing card 14 may include a plurality of tab 26 of a plurality of shapes, while in other examples backing card 14 may include a plurality of tabs 26 that all define relatively similar shapes.

Tabs 26 may be configured to extend away from major surface 36 of backing card 14. In some examples, all tabs 26 are configured to extend away from major surface 36 in a substantially similar direction. For example, all tabs 26 may be configured to extend generally in towards a geometric center of backing card 14 when backing card 14 is in its closed state 24. By configuring tabs 26 to generally point in towards a geometric center of backing card 14 (e.g., rather than out away from backing card 14), backing card 14 may reduce a number of physical features on which pouch 16 may catch. By reducing a number of features on which pouch 16 may catch, backing card 14 may be configured to promote an integrity of medical device 12.

Tabs 26 may define channels or hooks or slots or the like configured to engage with medical device 12 in order to secure medical device 12 to backing card 14. Each tab 26 may be configured to provide a securing force upon a received portion of medical device 12. The tabs 26 apply the securing force in a direction towards major surface 36 of backing card 14 (e.g., where the securing force may generally be oriented toward an end of tab 26 that is attached to major surface 36).

Once medical device 12 is secured to major surface 36 of backing card 14 by tabs 26, a user may place backing card 14 into pouch 16. Pouch 16 may be configured to provide a sealable compartment that may receive and fully encapsulate medical device 12 to protect and isolate medical device 12 during shipment and storage of medical device 12. In some examples, pouch 16 may be configured to define a completely sterile compartment by providing a hermetic seal and undergoing a sterilization procedure. Pouch 16 may be configured to seal shut once pouch 16 receives medical device 12. Pouch 16 may be configured to remain sealed until medical device 12 is removed from medical device package 10 (e.g., by a clinician in order for medical device 12 to be used in a medical procedure).

In some examples, as a result of backing card 14 being configured to move into the more compact closed state 24 as described herein, pouch 16 may define a predetermined size and shape that is substantially the same size as or slightly smaller than channel 34 of carton 20. As a result of pouch 16 being a predetermined size that is substantially the same size or slightly smaller than channel 34, medical device package 10 may reduce the likelihood that pouch 16 may be folded to be stored within medical device package 10. By reducing a likelihood that pouch 16 may be folded to fit within medical device package 10, medical device package 10 may reduce a likelihood that the integrity of pouch 16 will be adversely impacted as a result of folding as described herein, therein increasing an ability of medical device package 10 providing a sterile and physically robust compartment in which medical device 12 may be housed.

Pouch 16 may be a relatively flexible receptacle (e.g., a bag formed from a relatively flexible material) that is configured to receive and enclose (e.g., partially enclose or fully enclose) backing card 14 when backing card 14 is in closed state 24 and has received medical device 12. Pouch 16 may be formed from one or more of a film, a fabric made of flashspun HDPE fibers (e.g., Tyvek as manufactured by DuPont of Wilmington, Del.), a woven panel, a non-woven panel, a plastic panel, a polymer film, a paper film, a coated paper film, a metalized polymer film, a foil, a tray, a thermoform, a two-piece clamshell, or a folded clamshell. In some examples, pouch 16 is configured to define and maintain a hermetic seal around backing card 14.

Pouch 16 is configured to be opened by a clinician. For example, portion 28 of pouch 16 may be configured to be removed from pouch 16 (e.g., by being torn or cut off). In some examples, portion 28 of pouch 16 may be located at an end of pouch 16, such that portion 28 does not enclose any of backing card 14 (e.g., such that portion 28 of pouch 16 may be removed without requiring backing card 14 to be oriented away from portion 28 while portion 28 is being removed from pouch 16). Alternatively, in some examples pouch 16 may not include portion 28, but may instead be configured to be opened to expose backing card 14 and medical device 12 through alternate means. For example, pouch 16 may define a chevron pouch (e.g., a pouch with one or more outward-oriented chevron-shaped side walls) that may be opened without substantially contacting backing card 14, or pouch 16 may include an embedded pull string or wire that is configured to be removed to expose and remove backing card 14 and medical device 12, or pouch 16 may be configured to be cut open in any manner to expose and remove backing card 14 and medical device 12, or the like.

In some examples, pouch 16 may be manufactured from an opaque or transparent material. Configuring pouch 16 to be opaque or transparent may provide one or more advantages. For example, a fully or partially transparent pouch 16 may enable medical device 12 to be inspected when medical device 12 is within pouch 16, and, therefore, still sealed from environmental contaminants. Thus, a fully or partially transparent pouch 16 may enable medical device 12 to be inspected with less direct handling by a user.

After backing card 14 and medical device 12 are placed into pouch 16 (e.g., through an unsealed mouth of pouch 16 having one or more pre-sealed edges), pouch 16 may be sealed by sealing edge regions of pouch 16 (e.g., where edge regions are the two sides of the unsealed mouth). Pouch 16 may be included in a sterilization process as is discussed herein, such that medical device package 10 may be sterilized within pouch 16, whether before or after medical device package 10 is sealed within pouch 16. For example, medical device package 10 may be formed from a material configured to withstand being exposed to a predetermined sterilization temperature for a predetermined period of time. The predetermined sterilization temperature may be about 50° C. The predetermined period of time may be about 1 second, about 10 seconds, about 1 minute, about 30 minutes, about 1 hour, about 2 hours, or more than 2 hours. In some examples, in addition to, or instead of, exposing medical device package 10 and medical device 12 to the predetermined sterilization temperature, medical device package 10 may be configured to withstand other sterilization techniques. For example, medical device package 10 may be configured to withstand microwave, steam, ethylene oxide or ozone sterilization, or other sterilization techniques. In some examples, the sterilization may be performed after sealing backing card 14 and medical device 12 in pouch 16 of medical device package 10. In other examples, the sterilization may be performed before sealing backing card 14 and medical device 12 in pouch 16 of medical device package 10. After medical device package 10 receives medical device 12, the one or more unconnected edge regions of pouch 16 may be sealed, for example, by thermal sealing. Impulse sealing or constant heat sealing may be used to expose at least one of the edge regions to a predetermined sealing temperature that causes the first and second peripheral edge regions to seal, for example, by fusing or melting.

Figure 1B:
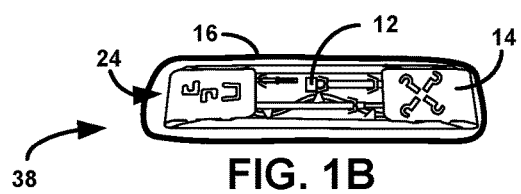
FIG. 1B is a conceptual and schematic diagram illustrating a loaded pouch that includes medical device and backing card sealed within the pouch of FIG. 1A.

FIG. 1B is a conceptual and schematic illustration of an assembly that includes sealed pouch 16 that is housing medical device 12 as secured to backing card 14 that is in closed state 24, said assembly referred to herein as loaded pouch 38 (e.g., where loaded pouch 38 refers to pouch 16 as receiving medical device 12 as secured to backing card 14 when backing card 14 is in closed state 24).

In some examples, medical device package 10 may include one or more additional components that facilitate the use of medical device 12. For example, looking back to FIG. 1A, medical device package 10 may include identification card 18. Identification card 18 may be a relatively flat component that is configured to be received within medical device package 10 and display information related to medical device 12 and/or medical device package 10. For example, identification card 18 may be a leaflet insert or the like, and may include information related to contents of medical device package 10, or information related to accessing, unpacking, or otherwise using medical device 12 stored within medical device package 10. Such information may alternatively or additionally be displayed on one or more labels affixed to pouch 16, backing card 14, and/or carton 20. In some examples, identification card 18 may be made of or coated with a material that can be written on, such that clinicians using or unpacking medical device 12 may write notes on identification card 18. Further, medical device package 10 may be configured such that identification card 18 is visually presented immediately upon opening medical device package 10. For example, being as medical device package 10 is a top-opening system as depicted in FIG. 1A, identification card 18 may be received within medical device package 10 on an X-Y plane with information displayed facing this "top" surface.

In the example shown in FIG. 1A, medical device package 10 includes carton 20. Carton 20 is configured to receive identification card 18 and loaded pouch 38. In some examples, carton 20 may be further configured to received identification card 18 and medical device 12 secured to backing card 14 in closed state 24 without pouch 16 encompassing backing card 14 and medical device 12.

In some examples, carton 20 may define most or all of the outermost surface of medical device package 10, therein providing an initial layer of protection between an external shipping and/or storage environment and medical device 12. Further, as discussed herein, carton 20 may be configured to function as a buffer that may absorb external forces applied to medical device package 10 such that loaded pouch 38 that is housed within carton 20 may receive less or none of the external forces as applied to medical device package 10. For example, carton 20 may be configured to define a buffer that comprises substantially empty space between the exterior perimeter as defined by carton 20 and loaded pouch 38 as received by and located within carton 20. In this way, carton 20 may be configured such that an external force applied to carton 20 may cause carton 20 to momentarily or permanently deform or crumple inward into the substantially empty space without applying much or any force onto loaded pouch 38. Configuring carton 20 to define the outer perimeter of medical device package 10 while also providing such a buffer between the outer perimeter and the received medical device 12 may improve an ability of medical device package 10 to provide and protect a sterile and/or physically secure compartment for medical device 12.

Carton 20 may be configured to be a top-loaded storage system. For example, carton 20 may be configured to rest on an X-Y plane when a user puts loaded pouch 38 into or takes loaded pouch 38 out of carton 20, where the user may retrieve loaded pouch 38 from or place loaded pouch 38 into carton 20 generally in a direction along the Z-axis. The user may place loaded pouch 38 into or take loaded pouch 38 from carton 20 in a direction generally along the Z-axis as a result of the carton 20 being configured to make loaded pouch 38 physically accessible in a direction along the Z-axis (e.g., when carton is resting on the XY plane). By configuring carton 20 to be a top-loaded storage system, carton 20 may improve an ease with which a user may handle, store, and retrieve loaded pouch 38 when carton 20 is in receiving state 22.

Carton 20 includes exterior walls 30A-30F (collectively "exterior walls 30") and a plurality of spacing elements 32A-32G (collectively "spacing elements 32"). In some examples, spacing elements 32 and exterior walls 30 may be made of the same material, such as a paper product or a polymer. For example, both exterior walls 30 and spacing elements 32 may be made of corrugated cardboard. Similar to backing card 14, carton 20 may be configured to be both relatively deformable (e.g., such that a clinician may bend or otherwise move portions of carton 20 in order to open carton 20 and access medical device 12 secured within carton 20) and relatively stiff (e.g., such that carton 20 may hold its shape, even in response to nominal forces such as gravity and incidental contact that is applied to carton 20). Carton 20 may be configured to be more stiff than backing card 14 (e.g., as a result of being thicker than backing card 14, or being constructed of a stiffer material). Configuring carton 20 to be relatively stiffer may improve an ability of carton 20 to protect medical device 12 from external forces (e.g., by providing a relatively "tough" outer boundary that may absorb or deflect these external forces).

Exterior walls 30 may define the outer bounds of medical device package 10 when medical device package 10 has received medical device 12 and carton 20 is in the storage state (not depicted). In these examples, when medical device package 10 is being stored and/or shipped, exterior walls 30 may be substantially the only components of medical device package 10 that are visible and/or immediately accessible, such that all or substantially most other components of medical device package 10 are securely contained within exterior walls 30.

Spacing elements 32 may be integral with or separate from and mechanically connected to exterior walls 30. For example, spacing elements 32 may be glued or otherwise mechanically or chemically secured to exterior walls 30. In some examples, some portions of spacing elements 32 may be integral with exterior walls 30, while other portions of spacing elements or glued or otherwise fastened to exterior walls 30. Spacing elements 32 may be formed from the same uniform piece/sheet of material as exterior walls 30.

A user may place loaded pouch 38 in channel 34 as defined by spacing elements 32 when carton 20 is in receiving state 22. Channel 34 may be configured to receive loaded pouch 38 at a static position (e.g., static relative to carton 20) within carton 20 that defines a threshold distance between all outer surfaces of loaded pouch 38 and the nearest respective inner surface of exterior walls 30 of carton 20. Further, channel 34 may define a shape that is substantially similar to a longitudinal profile of loaded pouch 38 and/or backing card 14 (e.g., channel 34 may define a rectangle with a substantially similar longitudinal length and width as backing card 14 and therein loaded pouch 38 as viewed normal to the central region of major surface 36). In some examples, channel 34 may define a shape that interconnects or mates with loaded pouch 38, including mating pairs of grooves, notches, ridges, or the like. Configuring channel 34 and loaded pouch 38 to interconnect or mate in this way may improve an ability of medical device package 10 to receive medical device 12 in a stable fashion (e.g., such that medical device 12 is less likely to move relative to medical device package 10 once received).

A depth of channel 34 as defined by spacing elements 32 may be adjustable based on the size of loaded pouch 38. In some examples, channel 34 as defined by spacing elements 32 may be substantially the same size or slightly larger or slightly smaller than the outer perimeter of loaded pouch 38, such that loaded pouch 38 is secured in substantially all directions and has little or no space to move within carton 20 when carton 20 is in the storage state. For example, one spacing element 32C may contact and engage a "bottom" surface of loaded pouch 38, while two spacing elements 32A, 32B may contact and engage a "top" surface (opposite the bottom surface) of loaded pouch 38, while two other spacing elements 32D, 32E may be configured to diagonally brace and engage a stabilizing force upon two ends of loaded pouch 38 (the ends extending between the top and bottom surface) by interfacing with two other spacing elements 32F, 32G that are attached to spacing elements 32A, 32B, and 32C.

In some examples, spacing elements 32 may be configured to engage loaded pouch 38 along the entirety of a length of loaded pouch 38, such that it may be difficult or impossible for loaded pouch 38 to pivot or twist within carton 20 without one or many of spacing elements 32 applying a countering force to loaded pouch 38 (e.g., a force that is opposed to the pivoting or twisting motion and that is configured to stabilize or immobilize the loaded pouch 38 relative to carton 20).

By configuring spacing elements 32 to engage loaded pouch 38 such that loaded pouch 38 has little or no space to move within carton 20 when carton 20 is in storage state, medical device package 10 may reduce a likelihood of relative motion between pouch 16, spacing elements 32, and backing card 14 as medical device package 10 is stored, shipped, and handled. By reducing a likelihood of relative motion between pouch 16, spacing elements 32, and backing card 14, medical device package 10 may reduce a chance that the structural integrity of pouch 16 will be adversely affected as a result of such relative motion, therein potentially increasing an ability of medical device package 10 providing a sterile and physically secure compartment in which medical device 12 may be shipped, stored, and/or handled.

Further, in some examples, spacing elements 32D, 32E may be further configured to engage a portion of spacing elements 32A, 32B, respectively, that is contacting a "bottom" exterior wall 30C. Spacing elements 32D, 32E may provide a downward securing force along the Z-axis on spacing elements 32A, 32B. As a result of the downward securing force applied to spacing elements 32A and 32B by spacing elements 32D and 32E, spacing elements 32A and 32B may further provide the downward stabilizing force upon the "top" surface of loaded pouch 38. In this way, carton 20 may be configured to have features of a "top" portion of carton 20 (e.g., outer spacing elements 32D, 32E as attached to top exterior wall 30A) contact other elements of carton 20 that provide a downward securing force throughout carton 20.

When a user moves carton 20 to a storage state, spacing elements 32 may secure loaded pouch 38 in a substantially stable and fixed position relative to carton 20. For example, when carton 20 is in the storage state, spacing elements 32 may define channel 34 with some substantially similar dimensions as loaded pouch 38, such that interior surfaces of spacing elements 32 contact exterior surfaces of loaded pouch 38. In this example of FIG. 1A, a user may place loaded pouch 38 on "bottom" spacing element 32C, after which the user may move two "top" spacing elements 32A, 32B over loaded pouch 38, after which the user may "close" the "top" exterior wall 30A to put carton 20 into the storage state (not depicted). As a result of spacing elements 32 defining channel 34 with substantially similar dimensions to loaded pouch 38, loaded pouch 38 may not have sufficient room to move more than a nominal amount in any direction relative to carton 20 once the user puts loaded pouch 38 within carton 20, even if carton 20 is dramatically moved in one or more directions. Therefore, once carton 20 is in the storage state and loaded pouch 38 is received in channel 34, loaded pouch 38 may be substantially secured in a single fixed position relative to carton 20 as a result of spacing elements 32 engaging loaded pouch 38 in a substantially uniform manner across most or all external faces of loaded pouch 38. As a result of spacing elements 32 engaging loaded pouch 38 in such a uniform manner, medical device package 10 may be configured to prevent the secured medical device 12 from pivoting or rotating around a single point and/or "twisting" within medical device package 10.

Further, as discussed herein, spacing elements 32 may be configured to define a "buffer" between loaded pouch 38 (and therein medical device 12) and exterior walls 30. For example, as a result of a relatively uniform height of backing card 14 (the height being measured along the Z-axis direction) when backing card 14 is in closed state 24 and spacing elements 32 extending out a relatively uniform amount from exterior walls 30 to engage loaded pouch 38, medical device package 10 may define a threshold amount of distance between the exterior surface of a received loaded pouch 38 and the nearest respective portion of exterior walls 30 of carton 20. Configuring carton 20, backing card 14, and pouch 16 such that carton 20 receives loaded pouch 38 at a stable and fixed location relative to carton 20 where exterior surfaces of loaded pouch 38 are not contacting exterior walls 30 of carton 20 may increase an ability of medical device package 10 to promote the integrity of the stored medical device 12 within loaded pouch 38 when carton 20 is in the storage state.

Figure 2:
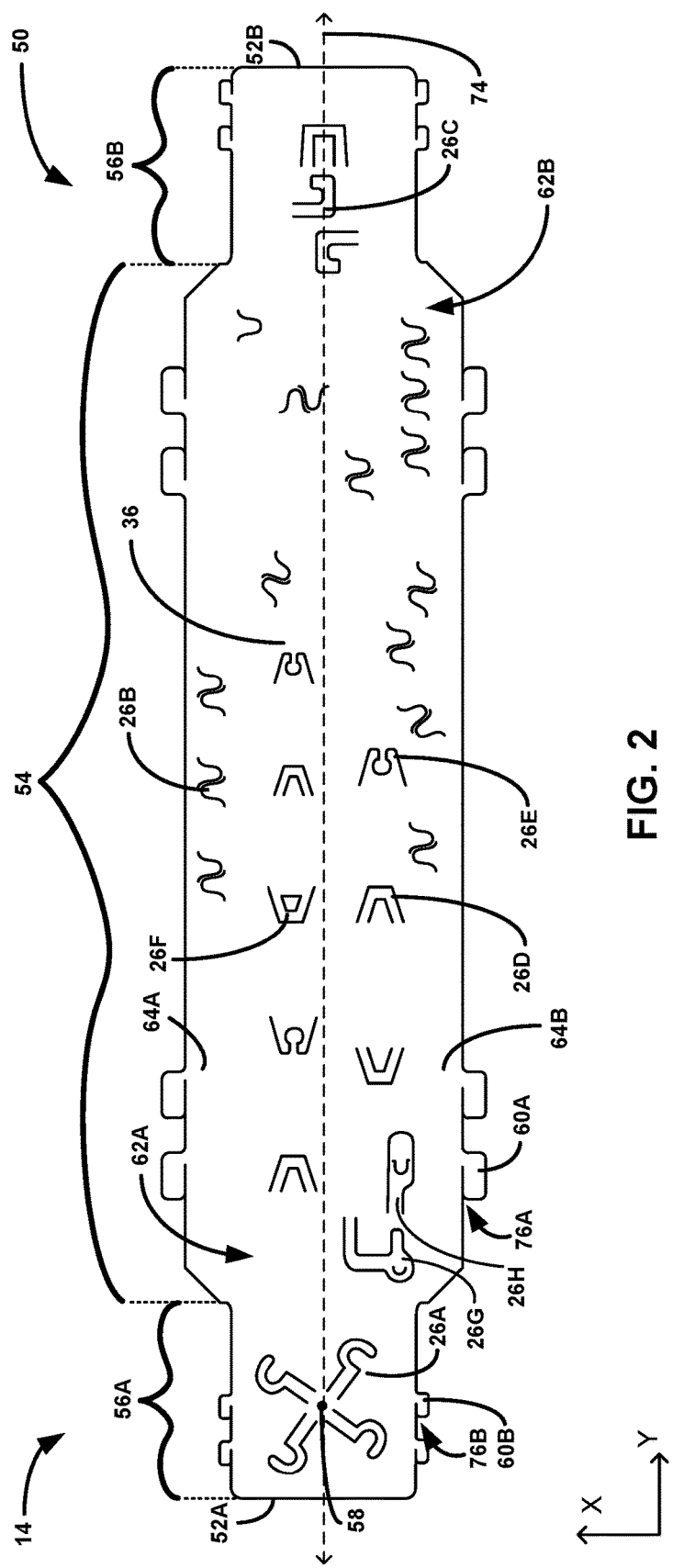
FIG. 2 is a conceptual and schematic diagram illustrating the backing card of FIG. 1A in an open state.

FIG. 2 is a conceptual and schematic diagram illustrating open state 50 of backing card 14 of FIG. 1A. The specific shape and arrangement of components of backing card 14 as depicted in FIG. 2 is for purposes of illustration only, and the same features or different features, or a greater or fewer number of features may be present in other backing cards 14. The specific configuration of backing card 14, including the relative dimensions, as well as the placement and number of tabs 26 and flaps 56, may depend upon the type and configuration of medical device 12 intended to be secured to backing card 14.

In some examples, backing card 14 may be manufactured into the depicted open state 50, such that backing card 14 is cut or otherwise removed from a large sheet of material in a shape that substantially resembles open state 50. As such, the depicted lines of the backing card 14 shown FIG. 2 may indicate cuts into the material, rather than creases or folds. In some examples, backing card 14 may contain relatively few or substantially no creases or folds.

Backing card 14 may include major surface 36 that extends along the X-Y plane. Major surface 36 may be a relatively flat surface as manufactured and in open state 50. In some examples, major surface 36 may be either of two surfaces of backing card 14, such that backing card 14 is "reversible" and either of two opposing surfaces may be used to receive medical device 12 as described herein. In other examples, one of the two substantially similar (e.g., by shape) surfaces of backing card 14 may be treated or coated with a material (e.g., such as the lubricious coating described above), such that the treated/coated surface is major surface 36.

As shown in FIG. 2, major surface 36 of backing card 14 includes central region 54 and one or more flaps 56A, 56B (collectively "flaps 56") that are on one or more ends of central region 54. For example, where backing card 14 defines longitudinal axis 74, flaps 56 may be extend from central region 54 out to both longitudinal ends 52A, 52B of backing card 14. In other examples, backing card 14 may include additional flaps 56 on one or more sides of central region 54, or only a single flap 56 extending from central region 54 out to one longitudinal end 52 of backing card 14, or backing card 14 may include a series of flaps 56 that, rather than being located on opposite ends of backing card 14, are arranged in a different manner around major surface 36 of backing card 14 (e.g., in a circular arrangement around an outer perimeter of backing card 14). Each of the additional flaps 56, however, may be configured to secure at least a portion of medical device 12 and move over at least a portion of central region 54 when backing card 14 is moved to closed state 24. Put differently, each flap 56 may be configured to reduce a footprint of backing card 14 as a result of a user moving the respective flap 56 to put backing card 14 into closed state 24.

In some examples, central region 54 of backing card 14 may be substantially similar (e.g., the same or nearly the same but for manufacturing variances) to flaps 56 of backing card 14 in terms of physical properties of backing card 14 (e.g., stiffness, height, etc.). In other examples, however, flaps 56 may have one or more different properties than central region 54. For example, flaps 56 may have a different height (e.g., as measured in the Z-axis direction) than central region 54, or flaps 56 may have a different coating or less or more coating than central region 54. In some examples, flaps 56 may have different properties in order to configure backing card 14 to better move into closed state 24 or hold closed state 24. Similarly, one or more flaps 56 may have different properties than other flaps 56 based on different uses of respective flaps 56. For example, where one flap 56 may have a relatively large number of tabs 26 that may extend away from flap 56 to secure a portion of medical device 12, the respective one flap 56 may be relatively thicker or be coated with a strengthening coat or the like to provide more rigidity and/or strength for the respective flap 56 to compensate for the loss of material as a result of the relatively large number of tabs 26.

In order to transform backing card 14 from open state 50 to closed state 24 (shown in FIG. 1A), a user may move flaps 56 at least partially over central region 54. For example, flaps 56A, 56B may be configured to move over portions 62A, 62B (collectively "portions 62") of central region 54, respectively. In some examples, when flaps 56 are moved over central region 54 such that backing card 14 is in closed state 24, surfaces of flaps 56 may face surfaces of central region 54, e.g., such that the surfaces of flaps 56 are substantially parallel with the surfaces of central region 54. Though a user may move backing card 14 to closed state 24 subsequent to receiving and securing medical device 12, the geometrical shape of closed state 24 may be substantially similar whether or not backing card 14 has received medical device 12, such that surfaces of central region 54 that are facing surfaces of flaps 56 may be parallel with each other whether or not backing card 14 has received and secured medical device 12.

As discussed above, tabs 26A-26H (collectively "tabs 26") are configured to secure medical device 12 to major surface 36. Tabs 26 may be on central region 54 as well as on flaps 56. In some examples, tabs 26 of different sizes and/or shapes may be configured to secure different portions of medical device 12, or tabs 26 of different sizes and/or shapes may be configured to secure medical device 12 in different manners. In this way, each tab 26 may be configured (e.g., through a size, shape, and relative alignment on backing card 14) to receive and secure a specific predetermined portion of medical device 12. For example, tabs 26 may be located and/or aligned on backing card 14 to receive and secure respective portions or components of medical device 12 on each flap 56 and to enable a user moving backing card 14 from open state 50 to closed state 24 and back (e.g., such that backing card 14 does not define tabs 26 to secure medical device 12 in a manner that impedes the motion of a "joint" of backing card 14 that may reduce or eliminate an ability of backing card 14 to move into closed state 24 and/or open state 50).

In some examples, backing card 14 may include more tabs 26 than necessary to secure medical device 12, in order to provide a user numerous options in how to secure medical device 12. However, in other examples, tabs 26 are each used to connect medical device 12 to backing card 14. Further, in other examples, backing card 14 may include different sets of tabs 26 that are configured to secure different medical devices 12, such that a user may use different sets of tabs 26 of a single backing card 14 to secure different medical devices 12. In this way, one type of backing card 14 may be used to package many different medical devices 12, thereby potentially reducing manufacturing costs for medical device package 10 and reducing the number of types of backing cards 14 required to be stored by a medical device packaging (e.g., manufacturing) facility.

As described above, in some examples, backing card 14 may include a plurality of tabs 26 that are substantially the same size and shape, as well as a plurality of tabs 26 that are relatively different sizes and/or shapes, or the like. For example, a plurality of tabs 26A may be arranged in a circular arrangement around central point 58. These tabs 26A may include a relatively straight section that is aligned extending radially out from central point 58 (e.g., central to the circular arrangement) on major surface 36 (e.g., as depicted on FIG. 2, tabs 26A may be located on flap 56A of major surface 36), and a hooked section at an end of the relatively straight section. In this way, a plurality of hooked tabs 26A may extend away from major surface 36 and hook around a far segment of a discrete component of medical device 12 (e.g., where the near segment is physical contacting major surface 36 at or near central point 58), securing the discrete component to backing card 14 at central point 58.

As another example, tab 26B may be cut from major surface 36 such that tabs 26B may be angled away from major surface 36. When angled from major surface 36, tabs 26B may be biased towards major surface 36, and, therefore, provide a realignment force towards major surface 36 as tabs 26B attempt to realign with major surface 36. In this way, a component (e.g., a tube or catheter or the like) may be placed between major surface 36 and one or two opposing tabs 26B that are angled away from major surface 36, and the realignment force applied by tabs 26B towards major surface 36 may help hold the component in place relative to backing card 14. In some examples, tabs 26C may be shaped as hooks of various shapes that are configured to extend away from major surface 36, or tabs 26D, 26E, 26F may be configured to define a hole or path through which a portion of medical device 12 may be routed to secure that portion (and adjacent portions) of medical device 12 to backing card 14. As discussed in greater detail in FIGS. 6A-6C, in other examples, two or tabs 26G, 26H may be configured to interlock to provide a stabilizing force for medical device 12.

Backing card 14 may include a set of side walls 64A, 64B (collectively "side walls 64"). Side walls 64 may be extend out from the sides of central region 54 along the X-Y plane, and may be configured to be moved by a user to along the Z-axis. For example, a user may curl side walls 64 up along the Z-axis relative to central region 54 when backing card 14 is in closed state 24. The user may curl side walls 64 up from central region 54 at around a 90° angle relative to central region 54. Side walls 64 may be configured to interact with flaps 56 to secure backing card 14 in closed state 24 (shown in FIG. 1A). In some examples, backing card 14 may define relatively fewer tabs 26 on side walls 64 to better configure backing card 14 to assume closed state 24 (e.g., where tabs 26 on side walls 64 may inhibit or prevent side walls 64 from extending along Z-axis at around the 90° angle).

For example, side walls 64 may include one or more flags 60A that mate with flags 60B of flaps 56 to hold both flags 60A, 60B in place in the closed state 24. Flags 60A, 60B (collectively "flags 60") may define respective slots 76A, 76B (collectively "slots 76") between flags 60 and respective side walls 64 and flaps 56. Flags 60 may be configured to interlock with each other by being received by slots 76 of complementary flags 60 to hold backing card 14 in closed state 24. For example, flags 60B and 60A may be complementary flags, such that flag 60B is configured to be received by slot 76A between flag 60A and side wall 64B while flag 60A is received by slot 76B between flag 60B and flap 56A. The interlocking configuration of flags 60 may help hold backing card 14 in closed state 24.

Figure 3C:
FIGS. 3A-3C are conceptual and schematic diagrams illustrating a view of two interlocking tabs of the backing card of FIG. 1A, and illustrate the interlocking tabs opposing each other, interfacing with each other, and interlocked, respectively.
Figure 3B:
Figure 3A:
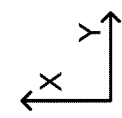

In some examples, tabs 26 may interface with each other. FIGS. 3A-3C depict two tabs 26I, 26J that are aligned opposite each other and are configured to mate (or interlock) together. Tabs 26I, 26J are examples of tabs 26 that may be used with backing card 14. In the example shown in FIGS. 3A-3C, tabs 26I, 26J define respective holes 66A, 66B (collectively "holes 66") that extend through a thickness of tabs 26I, 26J. The thickness of tabs 26I, 26J is measured in the Z-axis direction in FIG. 3A. Holes 66 may be configured to receive a portion of medical device 12. One relatively larger tab 26I may define straight slit 70 and curved slit 72, while relatively smaller tab 26J may define straight slit 73. Curved slit 72 may enable portion 75 of tab 26I that is generally within curved slit 72 to move along at least one axis relative to adjacent areas of tab 26I that are not within curved slit 72. Tabs 26I, 26J may be useful for locking a component of medical device 12 in place (e.g., a distal end of a catheter, as the distal end may otherwise move around and be difficult to secure).

To use tabs 26I, 26J, the relatively smaller tab 26J may be curled around and inserted through straight slit 70 of the relatively larger tab 26I, as depicted in FIG. 3B. A user may then curl larger tab 26I around and over smaller tab 26J, at which point portion 75 of larger tab 26I within curved slit 72 may be positioned at least partially into slit 73 of smaller tab 26J, as depicted in FIG. 3C. At this point, when tabs 26I, 26J are extended away from major surface 36, both holes 66 may at least partially align (e.g., partially align or fully align) to create a channel that may be used to lock and stabilize a component of medical device 12 in place. Configuring two or more tabs 26 to work together to stabilize a portion of medical device 12 may improve an ability of backing card 14 securing and stabilizing medical device 12.

Figure 4:
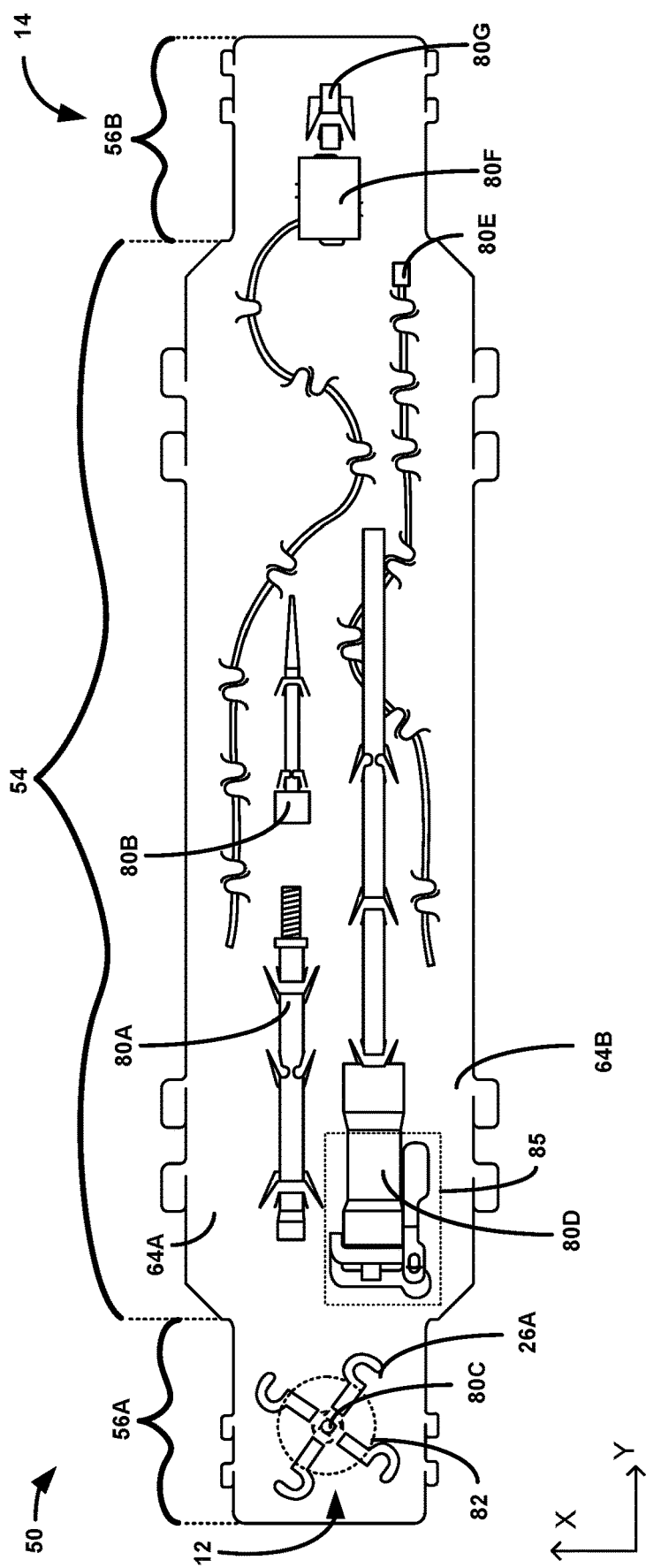
FIG. 4 is a conceptual and schematic diagram illustrating a plan view of the backing card as having received the medical device of FIG. 1A.

In some examples, medical device 12 may include a plurality of discrete components. For example, FIG. 4 is a conceptual and schematic diagram of backing card 14 of FIG. 1A in open state 50 as receiving a plurality of components 80A-80G (collectively "components 80") of medical device 12. The specific number and selection of components of medical device 12 is depicted for purposes of illustration only, as medical device 12 may include the same components 80 or different components 80 or a greater number or a fewer number of components 80 in other examples. Similarly, the specific alignment and manner as to how components 80 of medical device 12 are received by backing card 14 as depicted in FIG. 4 is for purposes of illustration only, as the alignment and manner of securing medical device components 80 may change in other examples based on both/either the specific components 80 of medical device 12 and the type and configuration of tabs 26 on backing card 14.

As depicted in FIG. 4 and discussed herein, components 80 of medical device 12 are received on and secured to both flaps 56 and central region 54 of backing card 14. Detail view 82 as depicted in FIGS. 5A-5C relates to tabs 26A securing medical device component 80C, while detail view 85 as depicted in FIGS. 6A-6C relates to the securement of medical device component 80D using tabs 26.

Figure 5A:
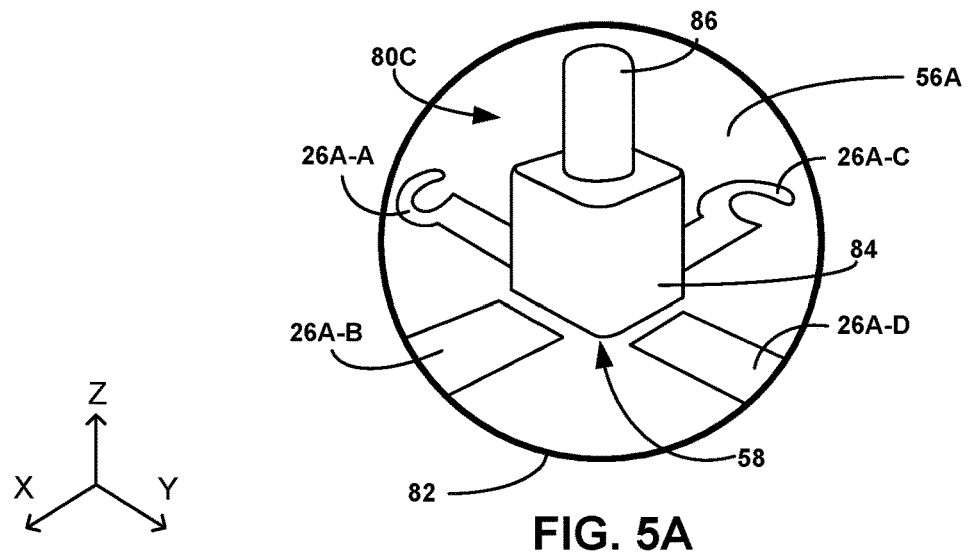
FIGS. 5A-5C are conceptual and schematic diagrams illustrating tabs of the backing card of FIG. 1A securing an example cylindrically-shaped medical device component.
Figure 5B:
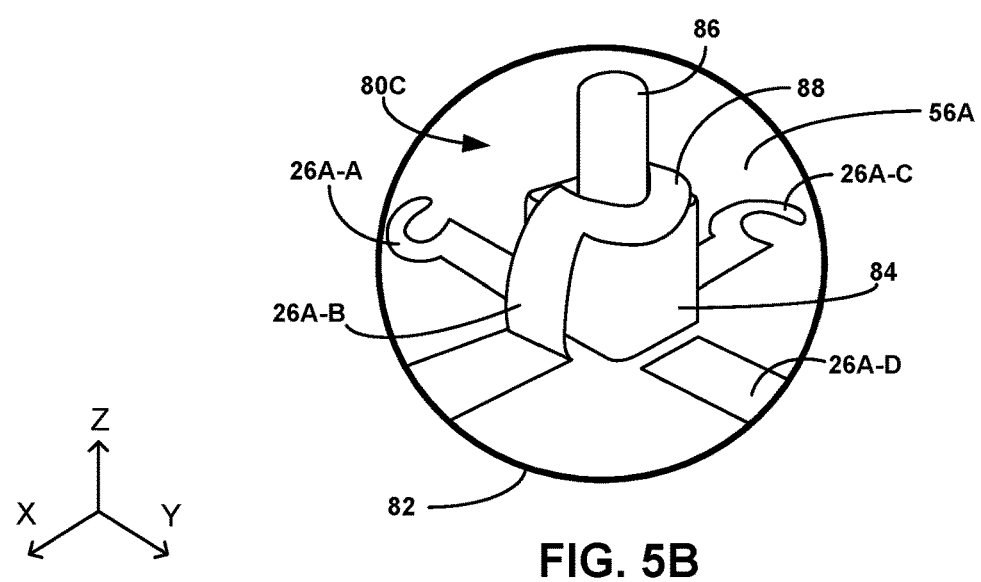
Figure 5C:
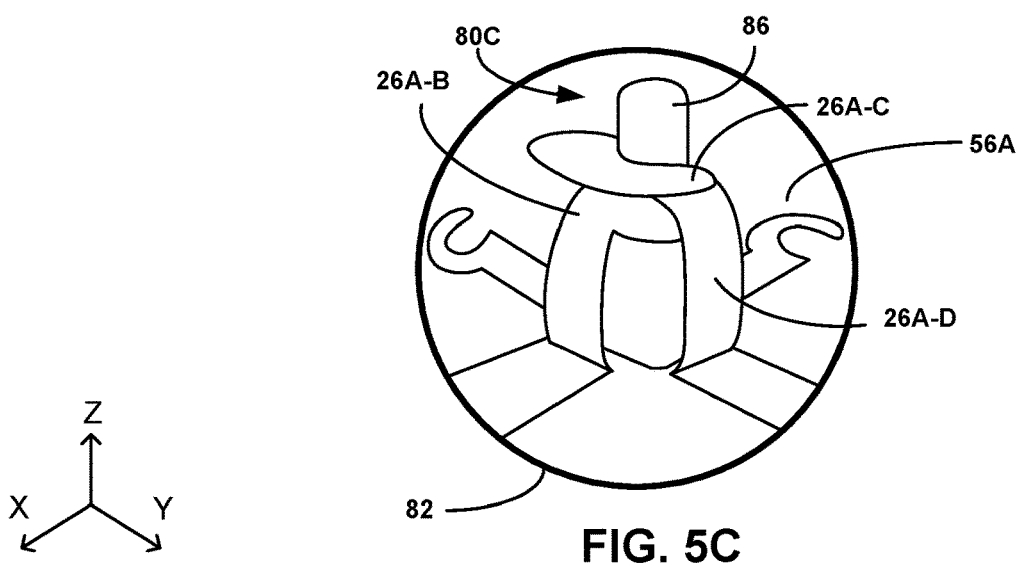

FIGS. 5A-5C are conceptual and schematic diagrams illustrating the detail view 82 of FIG. 4 of four tabs 26A-A, 26A-B, 26A-C, and 26A-D (collectively "tabs 26A") securing example cylindrical medical device component 80C, which is resting on the X-Y plane. Tabs 26A are depicted as being located on flap 56A such that medical device component 80C may be placed (e.g., by an assembling user) on central point 58 on flap 56A between tabs 26A, though it is to be understood that in other examples tabs 26A (and therein central point 58 and medical device component 80C) may be located and arranged at other portions of backing card 14. Medical device component 80C may include base 84 and knob 86. Once placed at central point 58, base 84 may contact flap 56A and extend along the X-axis away from flap 56A while knob 86 protrudes yet further (e.g., further than base 84 protrudes) along the Z-axis from a surface of base 84. As discussed herein, hooked portions of tabs 26A are configured to engage knob 86 to secure medical device component 80C to flap 56A (and therein backing card 14).

For example, as depicted in FIG. 5B, hooked portion 88 of tab 26A-B is extending along the Z-axis away from flap 56A and past base 84 to engage knob 86. A user or machine may move tab 26A-B such that the respective hooked portion 88 of tab 26A-B may engage knob 86 in the manner shown in FIG. 5B. As depicted in FIG. 5C, respective hooked portions 88 of each of the four tabs 26A may be used to engage knob 86. The tabs 26A may engage knob 86 in any order. In some examples, knob 86 may extend from a point on base 84 that is substantially centered on central point 58 (e.g., such that central point 58 and knob 86 are aligned along the Z-axis), such that each tab 26A may provide a substantially similar and consistent securing force on component 80C toward flap 56A. In this way, as viewed in FIG. 5C, tabs 26A may extend up along opposing walls or sections of base 84 to engage and secure knob 86, and therein medical device component 80C, to flap 56A of backing card 14.

Figure 6A:
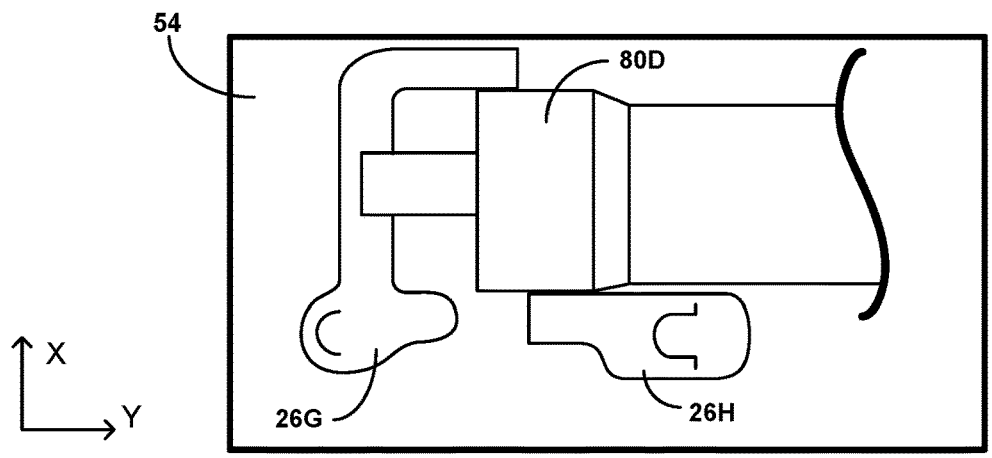
FIGS. 6A-6C are conceptual and schematic diagrams illustrating tabs of the backing card of FIG. 1A securing an example block-shaped medical device component.
Figure 6B:
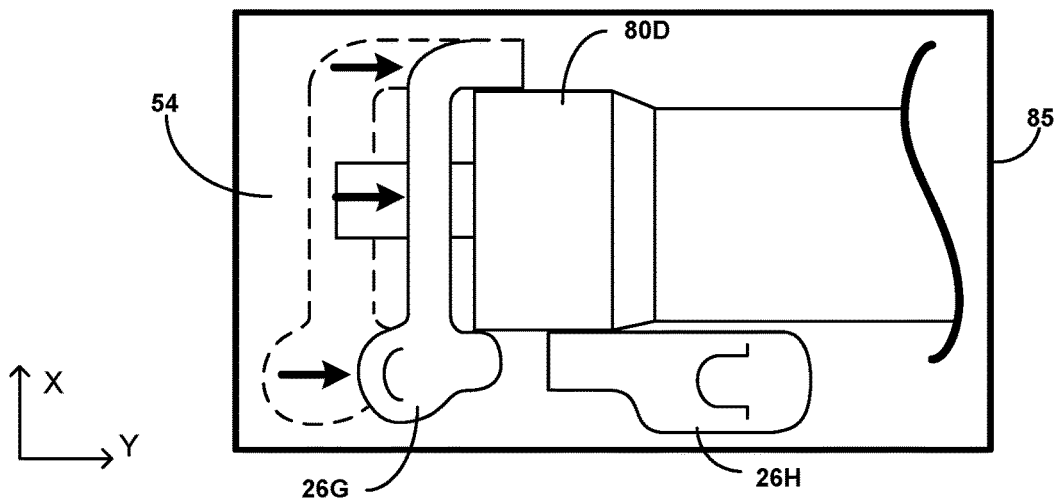
Figure 6C:
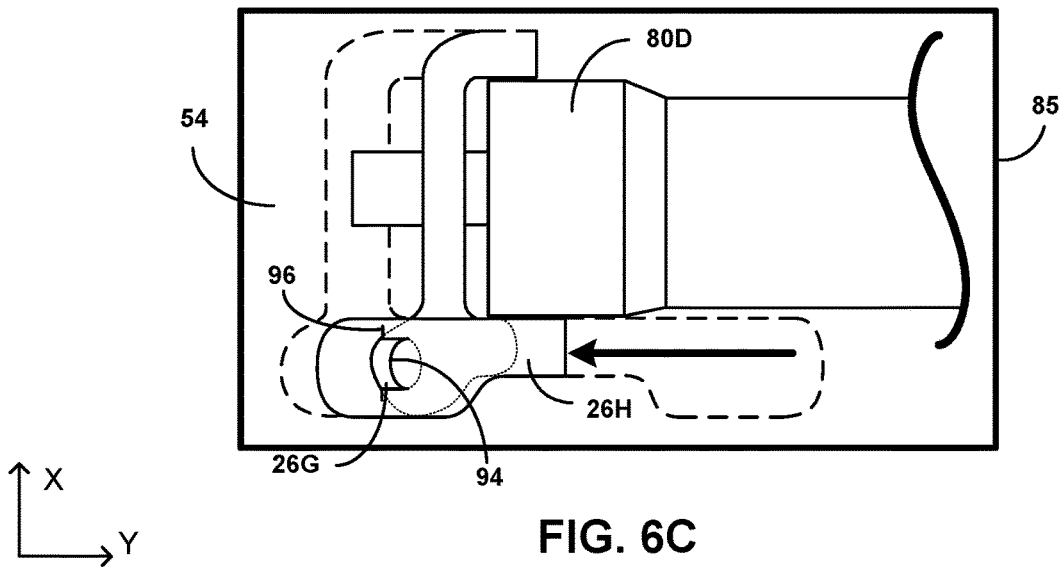

FIGS. 6A-6C are conceptual and schematic diagrams illustrating the detail view 85 of FIG. 4 of interlocking tabs 26G and 26H securing example block medical device component 80D, which is positioned on central region 54 of backing card 14 and on an X-Y plane. Tabs 26G and 26H are discussed and depicted as being located on central region 54 of backing card 14, though in other examples tabs 26G and 26H may be located on other portions of backing card 14.

A user may place medical device component 80D on central region 54 such that tab 26G extends across a width of medical device component 80D and tab 26H extends next to medical device component 80D substantially parallel with a longitudinal axis of medical device component 80D. The user may move tab 26G up in the Z-axis direction pivoting towards tab 26H while moving tab 26H up along the Z-axis direction pivoting towards tab 26G. Tab 26G may include slit 94 configured to receive tab 26H, and tab 26H may include slit 96 configured to receive tab 26G. As such, a user may pivot both tabs 26G, 26H along the Z-axis towards each other and such that both tabs 26G, 26H receive each other through respective slits 94, 96 while interlocking and receiving medical device component 80D. In certain examples, tab 26G may be configured to extend over a component or tube protruding from the longitudinal end of medical device component 80D, such that tab 26G is configured to be located within a crook between medical device component 80D and the protruding tube when a user interlocks tabs 26G, 26H. Tabs 26G, 26H may be configured to interlock in a shape that is substantially similar to a perimeter shape of medical device component 80D, such that tabs 26G, 26H interlock while contacting and securing medical device component 80D on all sides.

Figure 7A:
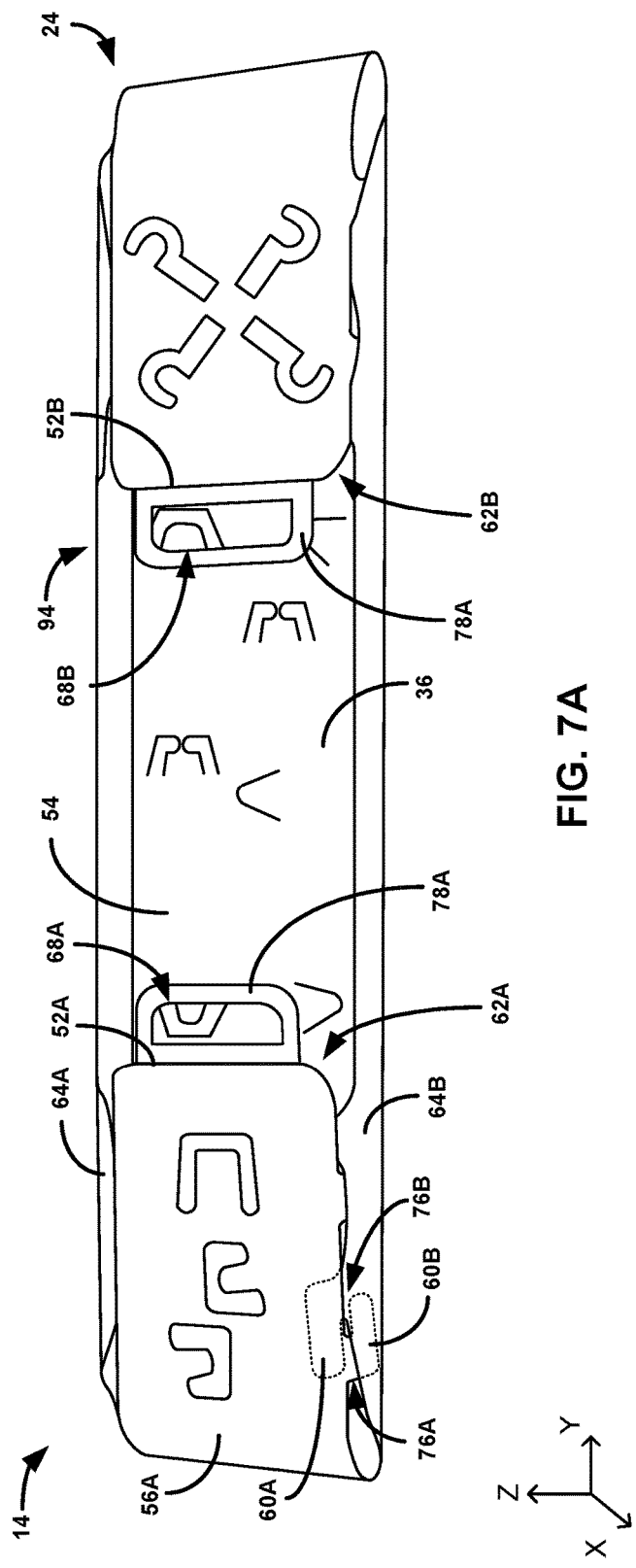
FIGS. 7A and 7B are conceptual and schematic diagrams illustrating perspective and side views, respectively, of the backing card of FIG. 1A in a closed state.
Figure 7B:
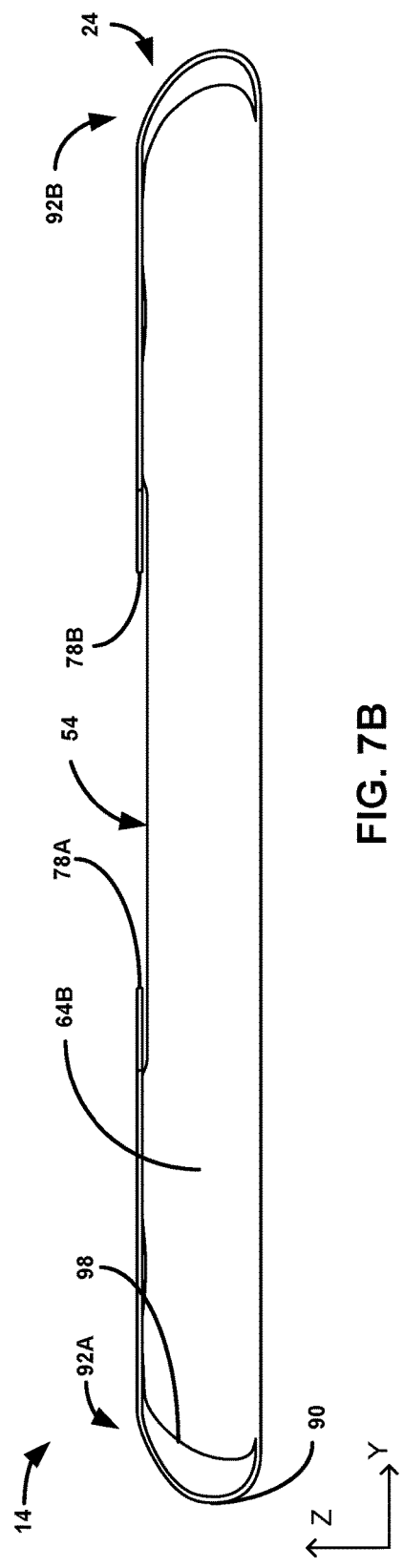

FIGS. 7A and 7B are conceptual and schematic diagrams illustrating perspective and side views, respectively, of backing card 14 in closed state 24. As depicted in FIG. 7A, in closed state 24, flaps 56 cover respective portions 62 of central region 54. The dotted lines of FIG. 7A depict hidden portions of flags 60. FIG. 7A depicts flag 60A extending from side wall 64B and interlocking with complementary flag 60B to help secure backing card 14 in closed state 24. As such, flag 60A may be received by slot 76B between flap 56A and flag 60B while flag 60B is received by slot 76A between side wall 64B and flag 60A.

In some examples, backing card 14 may include features or components that are configured to facilitate the handling of backing card 14. For example, as depicted in FIG. 7A, backing card 14 may include handles 78A, 78B (collectively "handles 78"). Handles 78 may define gaps 68A-68B (collectively "gaps 68") that may be sized to fit one or more fingers of a clinician looking to manipulate backing card 14. As such, backing card 14 may be configured such that backing card 14 may be removed from carton 20 and or placed by carton 20 using only handles 78 (e.g., such that handles 78 have sufficient attachment to backing card 14 to enable handles 78 to be used to handle backing card 14 without detaching from backing card 14). Handles 78 may extend longitudinally from longitudinal ends 52 of backing card 14. As such, in closed state 24, handles 78 may extend across an X-Y plane and partially cover central region 54. In some examples, handles 78 may be integral with backing card 14, such that handles 78 were formed with backing card 14. In other examples, handles 78 may be separate components that were attached or secured to backing card 14 (e.g., using an adhesive or the like).

As depicted in FIG. 7B, flaps 56 may be configured to move over central region 54 along a path that defines a curvilinear surface 90 as viewed from the side view of FIG. 7B. Flaps 56 may be configured to define this curvilinear surface 90 by the manner in which flaps 56 are attached to central region 54 and/or side walls 64. In some examples, backing card 14 may define curvilinear surfaces 90 in part or in whole as a result of material that is cut out from backing card 14 (e.g., as part of the assembly or manufacturing process), enabling backing card 14 to expand and interlock as depicted. For example, side wall 64B may define curvilinear edge 98 as a result of how side wall 64B is cut to extend in the Z-axis from central region 54. In this way, backing card 14 may be configured to avoid creating a sharp edge or corner at or near one or both longitudinal ends 92A, 92B (collectively "ends 92") of backing card 14 in closed state 24. In some examples, an outer perimeter of backing card 14 may substantially or exclusively define flat surfaces that intersect (e.g., meet or converge) to define such curvilinear surfaces 90 or curvilinear edges 98. Configuring backing card 14 to define relatively "soft" curves such as curvilinear surface 90 rather than a sharp (e.g., acute) edge at or near ends 92 may reduce a chance that backing card 14 punctures pouch 16, and may help reduce stress points between backing card 14 and pouch 16.

In some examples, backing card 14 is configured to substantially only define relatively flat surfaces and curvilinear surfaces 90 along an outer perimeter of backing card 14 when backing card 14 is in closed state 24 (e.g., such that substantially no edges or bends or corners are externally presented by backing card 14 when backing card 14 is in closed state 24). Reducing a chance that a shape of backing card 14 will puncture or otherwise adversely affect the integrity of pouch 16 may increase an ability of medical device package 10 housing, shipping, and/or storing medical device 12 in a manner that promotes the integrity of the stored medical device 12.

Further, as depicted in FIG. 7B, backing card 14 has a substantially uniform (e.g., uniform or within 20 millimeters) height in closed state 24 between ends 92 of backing card 14, the height being measured in the Z-axis direction. As a result of a substantially uniform height of backing card 14, it may be relatively easier for carton 20 to secure backing card 14 along a length of backing card 14, which may help reduce "up" and "down" movement along the Z-axis (e.g., movement that is generally perpendicular to central region 54) of backing card 14 (whether alone or when in pouch 16) relative to carton 20. This may help maintain the integrity of secured medical device 12.

Figure 8:
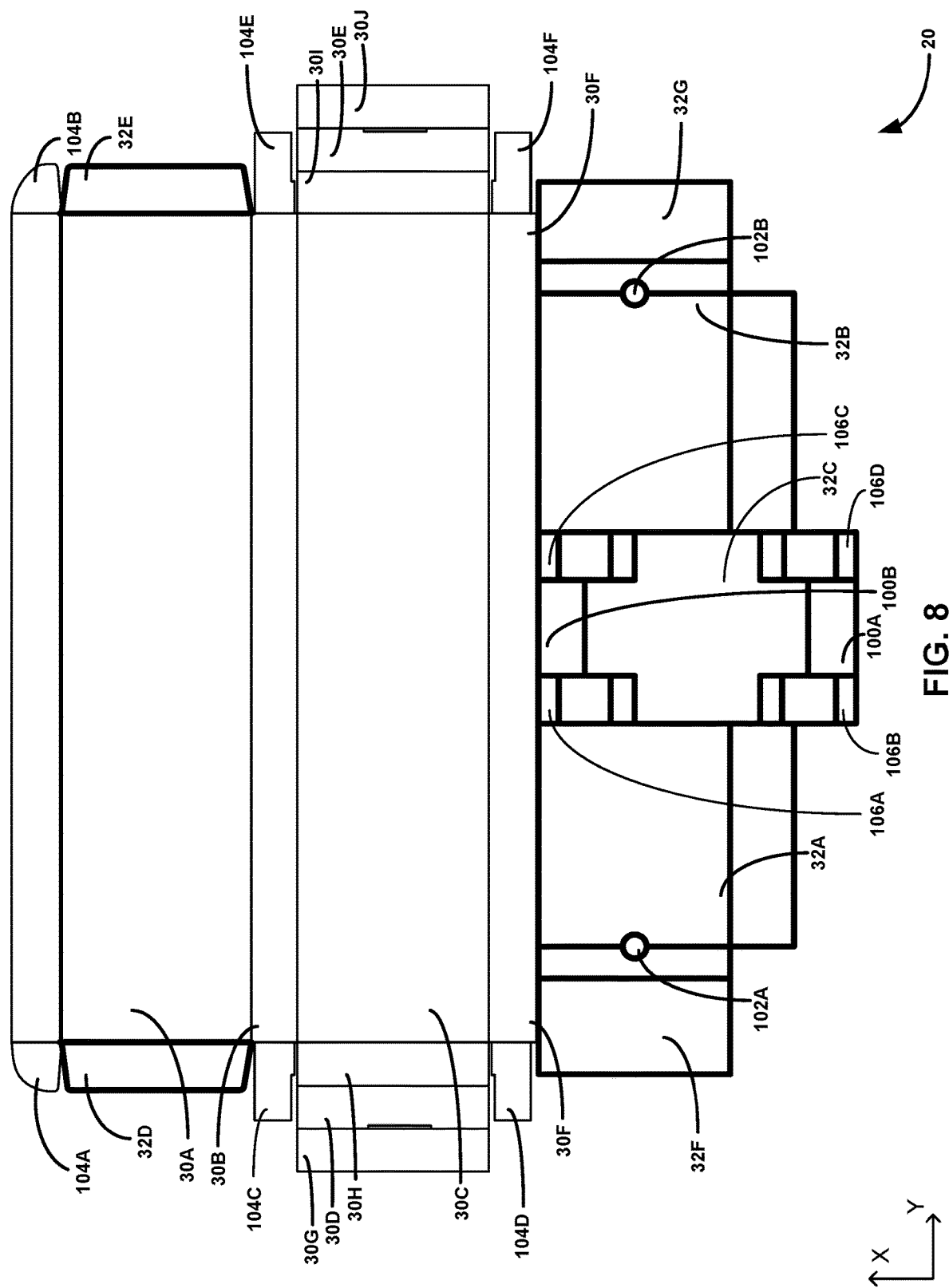
FIG. 8 is a conceptual and schematic diagram illustrating a plan view of the carton of FIG. 1A.

FIG. 8 is a conceptual and schematic diagram illustrating a plan view of example carton 20. The specific shape and arrangement of features of carton 20 as depicted in FIG. 8 is for purposes of illustration only, and, in other examples, carton 20 may have a different number of features or different features than that shown in FIG. 8. In some examples, lines of carton 20 as depicted in FIG. 8 may represent creases or folds of carton 20, and carton 20 may be folded (e.g., by a human operator or by a machine) along these lines to assemble carton 20 into receiving state 22 or the storage state. Folds of carton 20 may be created by a manufacturing machine or by a human operator or by some combination of the two.

As depicted in the plan view of FIG. 8, carton 20 may define a substantially similar height across the majority of carton 20 as measured along the Z-axis. Lines of spacing elements 32 are illustrated as relatively thicker in FIG. 8, to differentiate between exterior walls 30A-30J (collectively "exterior walls 30") that comprise the outer structure of carton 20 and the structures that comprise the spacing elements 32 that are configured to receive loaded pouch 38. In some examples, spacing elements 32 and exterior walls 30 may be made of a unitary structure or material, such as a single section or sheet of corrugated cardboard that the shape of FIG. 8 is cut or punched from. In other examples, carton 20 may be manufactured in one or more pieces, such that, for example, spacing elements 32 and exterior walls 30 may be separate components that are later connected. Where separate components of carton 20 are not assembled as a unitary structure but are attached to each after being formed, components of carton may be secured to each other using any suitable technique, such as, but not limited to, an adhesive. For example, an adhesive may attach spacing element 32C to exterior wall 30C, and the adhesive may be on a surface of flanges 100A, 100B to be secured to exterior walls 30F, 30B, respectively. In certain examples, carton 20 may be manufactured in a single piece, but some portions of carton 20 may still need to be securely attached to each other after being formed. For example, flange 100B may be formed as connected to exterior wall 30F, but flange 100A may need to be secured or otherwise fastened to exterior wall 30B as described herein.

In some examples, a relative location within carton 20 at which one or more of spacing elements 32 receives backing card 14 may be adjustable. For example, spacing element 32C may be configured to create channel 34 at different distances from exterior wall 30C, depending upon a general height of medical device 12, and/or backing card 14. For example, spacing element 32C may include adjustable sections 106A, 106B (collectively "adjustable sections 106"). Adjustable sections 106 may include available creases which could be used in assembling carton 20 into receiving state 22, where each crease resulted in a different relative height of spacing element 32 as measured along the Z-axis. In these examples, all adjustable sections 106 of a respective spacing element 32 may need to be folded at the same relative crease (e.g., a crease at the distance/height from bottom exterior wall 30C) to define a relatively flat channel 34 with which to receive backing card 14. Alternatively, backing card 14 and/or pouch 16 may have a relatively greater height near one end 92 (e.g., as a result of a relatively bulky portion of medical device 12 being located near that end 92). Therefore, one adjustable section 106 may need to be adjusted lower relative to a corresponding adjustable section 106 in order to keep medical device 12 level and/or secured across carton 20. Configuring carton 20 to include adjustable sections 106 may enable carton 20 to receive numerous different backing cards 14 of numerous different shapes and sizes, which may increase a versatility and reduce a manufacturing cost for creating cartons 20 for different medical devices 12.

In some examples, carton 20 may include one or more cutouts 102A, 102B (collectively "cutouts 102") to assist in handling carton 20. Cutouts 102 may include features such as holes, notches, grooves, or the like that are cut or punched out of carton 20 (e.g., such that no or relatively less material remains at the location of cutout 102 as a result of cutout 102). Cutouts 102 may enable a clinician to better manipulate features of carton 20 and/or medical device package 10.

Upon manufacturing/assembling plan view of carton 20 (e.g., by separately cutting exterior walls 30 and spacing elements 32 from sheets of corrugated cardboard, and then gluing exterior walls 30 to spacing elements 32), a user may fold carton 20 along the depicted lines of carton 20 of FIG. 8 to assemble carton 20 in receiving state 22. Carton 20 may be manufactured with the creases/lines of FIG. 8, such that an operator may consistently and reliably assemble carton 20 in receiving state 22 by folding carton 20 according to these creases/lines.

In some examples, exterior walls 30 of carton 20 may define substantially rectangular shapes. In some examples, substantially all exterior walls 30 of carton 20 may define substantially rectangular shapes, such that carton 20 defines an orthotope when fully assembled into the storage state. Configuring carton 20 to define an orthotope shape upon receiving medical device 12 and being assembled into the storage state may improve an ability of medical device package 10 to be efficiently stored and shipped, as a plurality of cartons 20 may be more efficiently stored and manipulated and shipped in an orthotope shape (e.g., in comparison to a rounded shape or a curved shape).

In some examples, carton 20 may include securing elements 104A-104F (collectively "securing elements 104"). Securing elements 104 may be configured to be received by corresponding slots (e.g., slots 122A, 122B of FIG. 9A) that may be defined by exterior walls 30 when carton 20 is in receiving state 22 and/or in storage state (e.g., such that slots are not yet defined when carton 20 is in the unassembled plan view of FIG. 8). When received by these slots, securing elements 104 may stabilize carton 20 in the respective state (e.g., receiving state 22 or a storage state). For example, securing elements 104 may stabilize carton 20 in the respective state when in storage and/or when handled by a user that is grasping exterior walls 30 of carton 20. Securing elements 104 may be configured to require a moderate amount of force to manipulate securing elements 104 into slots and/or to remove securing elements 104 from slots. For example, securing elements 104 may be configured to require an amount of force that is easily provided by a clinician that is attempting to open carton 20, while not easily provided by dropping medical device package 10.

In some examples, exterior walls 30 may be configured to fold or bend over each other near the longitudinal ends of carton 20, therein providing relatively more stiffness, cross-sectional width, and therein strength to the longitudinal ends of carton 20. For example, as depicted in FIG. 8, exterior walls 30G, 30D, and 30H extend from exterior wall 30C. When being assembled (e.g., assembled into receiving state 22), a user may bend/move exterior wall 30H up along the Z-axis at an approximately 90° angle relative to exterior wall 30C, after which the user may bend/move exterior wall 30D back down towards exterior wall 30C along the Z-axis at an angle substantially parallel with exterior wall 30H, after which the user may bend/move exterior wall 30G along the Y-axis to assume an approximately 90° angle relative to exterior wall 30D, such that exterior wall 30G is substantially parallel with exterior wall 30C. Further, in some examples, carton 20 may be configured to include securing elements 104C-104F that may be received by a slot defined by exterior walls 30 bending over each other. For example, a user may arrange securing elements 104C and 104D parallel with exterior wall 30H once exterior wall 30H is bent up along the Z-axis to assume the approximately 90° angle relative to exterior wall 30C, such that exterior wall 30D would bend over (and, along with exterior wall 30H, encompass) securing elements 104C and 104D once the user bent exterior wall 30D back towards exterior wall 30C.

FIGS. 9A and 9B are conceptual and schematic diagrams of medical device package 10 in which carton 20 has received identification card 18 and loaded pouch 38 before and after exterior wall 30A has closed to move carton 20 into storage state 140, respectively. Loaded pouch 38 and identification card 18 are received within (now-enclosed) channel 34 defined by of spacing elements 32. FIG. 9A includes cross-sectional line 120-120 that bisects medical device package 10, and FIG. 9B includes cross-sectional line 128-128 that bisects medical device package 10. As depicted in FIG. 9A, spacing elements 32A, 32B encloses a "top" side of loaded pouch 38, while spacing element 32C encloses a "bottom" side of loaded pouch 38, where top and bottom are relative to the view of FIG. 9A.

Further, as depicted in FIG. 9A and as a result of carton 20 being top-opening as discussed herein, identification card 18 may be within a clinician's view upon opening carton 20 (e.g., opened from storage state 140 by a clinician), such that documentation displayed upon identification card 18 is immediately identifiable. Further, by locating identification card 18 between loaded pouch 38 and one or more exterior walls 30A of carton 20, medical device package 10 may further promote the integrity of the received medical device 12 (e.g., by having another layer of protection between medical device 12 and external forces).

Exterior wall 30A of carton 20 may be folded down towards loaded pouch 38 to assemble carton 20 into storage state 140 of FIG. 9B that substantially entirely encloses backing card 14. Upon folding exterior wall 30A of carton 20 towards loaded pouch 38, securing elements 104A, 104B may be received by slots 122A, 122B, respectively, to secure carton 20 in storage state 140. Spacing elements 32D, 32E may occupy gaps 124A, 124B (collectively "gaps 124") that are adjacent ends 92 of loaded pouch 38 when loaded pouch 38 is received by spacing elements 32A, 32B, 32C. For example, spacing elements 32D, 32E may be configured to extend diagonally along the Z-axis direction from a "top" exterior wall 30A to a "bottom" exterior wall 30C across gaps 124 (e.g., as viewed in FIG. 11), therein contacting and bracing spacing elements 32A, 32B in place. In this way, carton 20 may include spacing elements 32 that occupy space between loaded pouch 38 and exterior walls 30 in substantially every direction relative to backing card 14.

The relative size of components of medical device package 10 are for purposes of illustration only, as components may be other sizes or shapes in other examples. For example, in some examples backing card 14 and therein loaded pouch 38 may have a shorter longitudinal length along longitudinal axis 126 of medical device package 10 (e.g., as a result of medical device 12 being relatively shorter or otherwise smaller), in response to which spacing elements 32D, 32E may be relatively longer to occupy the relatively larger gap 124 between backing card 14 and exterior walls 30E and 30D, respectively. Alternatively, a longitudinal length of carton 20 (e.g., a length of exterior walls 30A, 30B, 30C, 30F) may be reduced to accommodate a smaller backing card 14 and therein a smaller loaded pouch 38.

Figure 10:
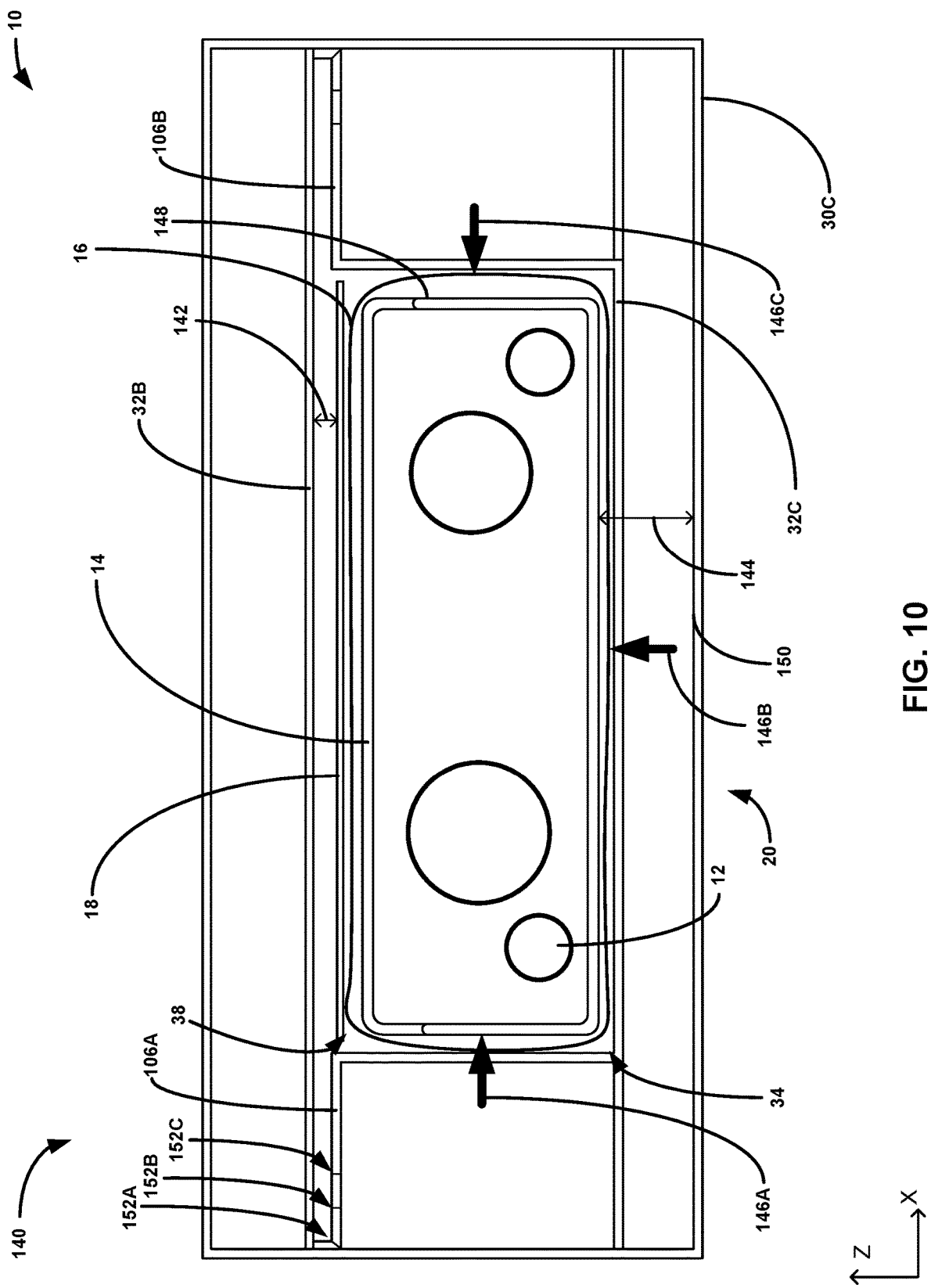
FIG. 10 is a cross-sectional side view of the identification card, backing card, and pouch received in the carton, where the cross-section is taken along line 120-120 in FIG. 9A.

FIG. 10 is a conceptual and schematic diagram illustrating a cross-sectional view of medical device package 10 including identification card 18, pouch 16 (in which medical device 12 and backing card 14 are received), and carton 20, where the cross-section is taken along line 120-120 of FIG. 9A. In the example shown in FIG. 10, carton 20 is in storage state 140. When in storage state 140, spacing elements 32 may provide one or more inward securing forces 146A-146C (collectively "inward securing forces 146") upon one or many or all outer surfaces 148 of backing card 14 and/or pouch 16. For example, adjustable section 106A of spacing element 32C may provide inward securing force 146A along the X-axis direction toward loaded pouch 38, a "bottom" section of spacing element 32C may provide inward securing force 146B along the Z-axis direction toward loaded pouch 38, and adjustable section 106B of spacing element 32C may provide inward securing force 146C along the X-axis direction toward loaded pouch 38.

In some examples, as depicted, there may be a small amount of unobstructed (e.g., unoccupied by a component of medical device package 10) space 142 between some portions of inner surfaces of one or more spacing elements 32B and one or more of backing card 14, pouch 16, and identification card 18, such that backing card 14, pouch 16, and/or identification card 18 may move some amount within carton 20 when carton 20 is in storage state 140. In other examples (not depicted), there may be substantially no unobstructed space 142 between inner surfaces of spacing elements 32 and one or more of backing card 14, pouch 16, and identification card 18, such that each outer surface 148 of backing card 14 has a substantially constant inward force 146 applied to these outer surfaces 148 by a respective spacing element 32.

When carton 20 is in storage state 140, outer surfaces 148 of backing card 14 may be at least threshold distance 144 away from inner surfaces 150 of exterior walls 30 along an entire perimeter of backing card 14. The depicted threshold distance 144 is for purposes of illustration only, as in other examples threshold distance 144 may be greater or smaller, or greater in some directions and smaller in other directions. For example, medical device package 10 may be configured to define a relatively greater threshold distance 144 where medical device 12 is relatively fragile, and medical device package 10 may be configured to define a relatively smaller threshold distance 144 where medical device 12 is relatively robust. In some examples, threshold distance 144 between at least one outer surface 148 of backing card 14 and at least one inner surface 150 of exterior walls 30 may be substantially similar to the combined cross-sectional thickness of pouch 16 and a respective spacing element 32 (e.g., such that backing card 14 is functionally lying against at least one exterior wall 30).

FIG. 10 further depicts creases 152A-152C (collectively "creases 152") of adjustable sections 106 of spacing elements 32. As depicted, adjustable section 106 of spacing element 32 is currently folded at crease 152A, which locates channel 34 at a maximum distance away from "bottom" exterior wall 30C. If adjustable section 106 were instead folded at crease 152B, then spacing element 32 and therein channel 34 would drop down, such that there would be relatively less distance between channel 34 and exterior wall 30C. If, for example, medical device 12 and/or backing card 14 had a height of a relatively greater magnitude, then a user may thusly use adjustable section 106 to lower channel 34 to allow for a relatively larger medical device 12, therein reducing the respective threshold distance 144 at the same time. Configuring carton 20 to include adjustable sections 106 that may change a relative height at which backing card 14 is received within carton 20 may provide more versatility to carton 20, such that a same carton 20 can be used for a variety of medical devices 12.

Figure 11:
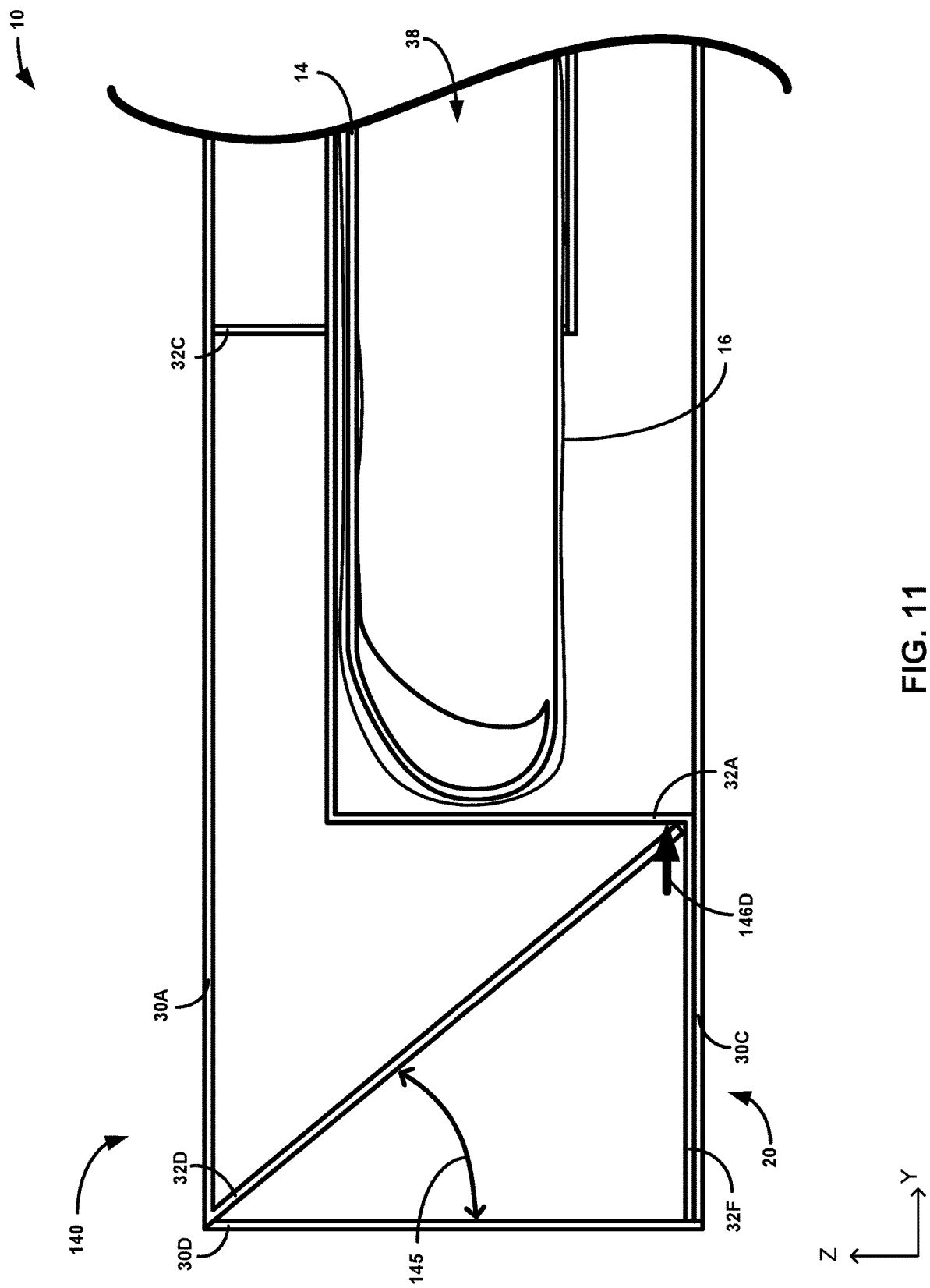
FIG. 11 is a partial cross-sectional view of the backing card and pouch as received in the carton, where the cross-section is taken along line 128-128 in FIG. 9B.

FIG. 11 is a conceptual and schematic diagram illustrating a cross-sectional view of medical device package 10 including loaded pouch 38 and carton 20 where the cross-section is taken along line 128-128 of FIG. 9B. FIG. 11 depicts orthogonal x-y-z axes, and a "bottom" exterior wall 30C of carton 20 is resting on the X-Y plane. In the example shown in FIG. 11, carton 20 is in storage state 140, such that loaded pouch 38 is received by spacing elements 32. Further as depicted in FIG. 11, spacing element 32D is extending diagonally at a generally 45° angle to the Z-axis between the "top" exterior wall 30A and the "bottom" exterior wall 30C. Spacing element 32D may extend between exterior walls 30 at different angles relative to Z-axis in other examples for other medical device packages 10. Spacing element 32D may be configured to extend from an outer exterior wall 30D to spacing element 32A to provide inward securing force 146D to loaded pouch 38 through spacing element 32A.

Further, as depicted in FIG. 11, spacing element 32F may extend along longitudinal axis 126 of medical device package 10 (e.g., as depicted in FIG. 9A) from spacing element 32A to longitudinal exterior wall 30D. By extending longitudinally between spacing element 32A and exterior wall 30D, spacing element 32F may further provide inward securing force 146D to loaded pouch 38 through spacing element 32A. Spacing element 32D may define angle 145 between itself and longitudinal exterior wall 30D in extending to spacing element 32A. In some examples, spacing element 32D may vary a length and/or may be configured to define different angles 145 in extending to spacing elements 32A. In some examples, spacing element 32D may be configured to define substantially any angle 145 between 0° (e.g., such that spacing element 32D is substantially parallel with longitudinal exterior wall 30D) and 90° (e.g., such that spacing element 32D is substantially parallel with top exterior wall 30A). Configuring spacing element 32D to define different angles 145 and/or be of different lengths in extending to spacing element 32A may enable spacing element 32D to occupy different positions, and, therefore, apply different inward securing forces 146D to accommodate different medical devices. This may help improve an ability of medical device package 10 to stably receive a particular medical device 12.

In some examples, rather than configuring spacing elements 32D, 32E to extend across gaps 124 and therein securing longitudinal ends of loaded pouch 38, medical device package 10 may instead include separate and discrete components configured to be inserted into and therein occupy gaps 124.

For example, FIGS. 12A and 12B are conceptual and schematic diagrams illustrating a plan and perspective view of box support 130 that may be used to secure medical device 12 within medical device package 10 of FIG. 1A by substantially filling gaps 124 at longitudinal ends of carton 20. Box support 130 may be made of any of the materials discussed herein. In some examples, box support 130 is made in substantially the same manner and out of the same materials as carton 20. For example, box support 130 may be stamped or cut from a sheet of corrugated cardboard, after which box support 130 may be assembled into support state 132 of FIG. 12B.

Box supports 130 may include a plurality of width sections 136A-136B (collectively "width sections 136") and a plurality of height sections 134A-134B (collectively "height sections 134"). Width sections 136 may define a shape that is substantially similar to a shape of one or more gaps 124 along the X-Y plane (e.g., a "top-down" shape, similar to the view of FIG. 9A), while height sections 134 may define a shape that is substantially similar to a cross-sectional shape of one or more gap 124 along the X-Z plane (e.g., a side shape, similar to the view of FIG. 10). Box support 130 may include alternating width sections 136 and height sections 134, such that when each section 134, 136 of box support 130 are bent to a substantially 90° angle relative to respective adjacent sections 134, 136, box support 130 may define a three-dimensional shape and size that is substantially similar to each of gaps 124.

In some examples, box support 130 may include one or more support sections 138A-138C (collectively "support sections 138") that are configured to extend within an internal space of box support 130 that is defined when box support 130 is in support state 132. One support section 138B may be configured to extend diagonally across the internal space of box support 130 when box support 130 is in support state 132, while two other support sections 138A, 138C may be configured to extend along a Z-axis direction next to both height sections 134 of box support 130 when box support 130 is in support state 132. For example, when a user assembles box support 130 into support state 132, first support section 138A may connect to width section 136B that is located in the X-Y plane and brace against height section 134A while extending in the Z-axis direction, while second support section 138B connects to first support section 138A and extends diagonally across internal space of box support 130, and third support section 138C connects to second support section 138B and braces against height section 134B while extending in the Z-axis direction.

One or more sections of box support 130 may include one or more cutouts 135A, 135B (collectively "cutouts 135"). For example, width section 136A may include a half-circle cutout 135A along a seam with height section 134B, while third support section 138C includes a H-shaped cutout 135B generally centered within third support section 138C. Box support 130 may include one or more cutouts 135 at locations where box support 130 is likely to be handled, such that it is easier for a user to assemble box support 130 or place box support 130 within or remove box support 130 from carton 20 when carton 20 is in receiving state 22.

FIG. 13 is a conceptual and schematic diagram illustrating a perspective view of identification card 18, loaded pouch 38, and two box supports 130A-B (collectively "box supports 130") as positioned within carton 20 of FIG. 1A. As depicted in FIG. 13, cutouts 135 of box supports 130 may be configured to align with cutouts 102 of carton 20 to facilitate the insertion and removal of box supports 130 from carton 20 in receiving state 22. In examples in which medical device package 10 is relatively heavy (e.g., as a result of a relatively heavy medical device 12), box supports 130 may improve an ability of medical device package 10 to absorb forces upon medical device package 10. By improving an ability of medical device package 10 to absorb forces, medical device package 10 may improve an ability to reduce or eliminate adverse effects of dropping medical device package 10 (e.g., where these effects might be relatively more pronounced where medical device package 10 is relatively heavier).

As discussed above, in some examples, an outer housing different than carton 20 may be used to house backing card 14 to which medical device 12 is connected. For example, backing card 14 may be positioned within a tray.

FIGS. 14A and 14B are conceptual and schematic diagrams illustrating an example medical device package 210 that includes tray 212 defining recess 208 configured to receive backing card 214, and film 216 that seals backing card 214 within recess 208. Backing card 214 may be substantially similar to backing card 14 with the exception of any differences discussed herein. FIGS. 14A and 14B depict orthogonal x-y-z axes, wherein medical device packages 210 are resting on a substantially flat X-Y plane and extending along the Z-axis direction away from the X-Y plane. Film 216 may be any material or layer that is capable of sealing backing card 214 within recess 208. In some examples, a user may place film 216 over a mouth of recess 208 once the user has loaded backing card 214 into recess 208 to hermetically seal backing card 214 within recess 208. Thus, in some examples, backing card 214 is housed within tray 212 and film 216 without first being introduced in pouch 16. That is, medical device package 210 may not include pouch 16 within recess 208. Upon receiving and sealing backing card 214 within recess 208, tray 212 may be received within carton 20, though in other examples, tray 212 is stored and shipped without carton 20.

In some examples, backing card 214 may include one or more features that facilitate the securement of backing card 214 within tray 212. For example, backing card 214 may include flags 260A, 260B (collectively "flags 260") of backing card 214 that are configured to extend away in a direction along the X-axis or Y-axis (e.g., a direction other than upwards towards film 216) away from central region 254. Flags 260 may be configured to mate or otherwise interlock with tray 212 to secure and/or lock backing card 214 in place relative to tray 212. Flags 260 may interface and/or mate with tray 212 in any manner. For example, flags 260A, 260B may be received by slits 226A, 226B carved into tray 212, respectively. In other examples, flags 260 of backing card 214 may interface and/or mate with features that extend out from tray 212 (e.g., extend along the Y-axis or X-axis). In some examples, backing card 214 may define one or more cutouts 228A, 228B (collectively, "cutouts 228") adjacent to flags 260A, 260B to potentially improve an ability of flags 260 flexing along the XY plane relative to backing card 214. Configuring backing card 214 to include features such as flags 260 that may interlock with features of tray 212 may improve an ability of medical device package 210 to secure backing card 214 in a single relative location in tray 212. In other examples, cut-outs 228 and/or one or more features of tray 212 may be configured such that the one or more features of tray 212 directly interface with cut-outs 228 to improve an ability of tray 212 to secure backing card 214 along the XYZ planes once backing card 214 is received by tray 212. Put differently, in some examples, one or more features of tray 212 may be configured to apply a stabilizing force to backing card 214 through cut-outs 228. In these examples, the stabilizing force may maintain backing card 214 in a position within tray 212 once backing card 214 is received by tray 212, such that backing card 214 is relatively less likely to move relative to tray 212 as a result of the stabilizing force.

FIG. 14B is a conceptual and schematic cross-sectional view of medical device package 210, where the cross-section is taken along line 218-218 of FIG. 14A. As shown in FIG. 14B, depth 220 of recess 208 measured along the Z-axis direction may be at least as great as height 222 of backing card 214, such that backing card 214 fits entirely within recess 208 of tray 212. Further, in some examples, tray 212 may define unobstructed space 224 between outer surfaces 248 of backing card 214 and the inner surfaces of tray 212, such that backing card 214 may have some amount of room in which to move subsequent to being placed in tray 212 by a user. Configuring tray 212 to define unobstructed space 224 may improve an ease with which a user may place backing card 214 within recess 208 and subsequently retrieve backing card 214 from recess 208. In other examples, tray 212 may define substantially no unobstructed space 224 between outer surfaces 248 of backing card 214 and the inner surfaces of tray 212, such that a position of backing card 214 is substantially fixed within tray 212 upon a user placing and sealing backing card 214 into recess 208 of tray 212.

Figure 15A:
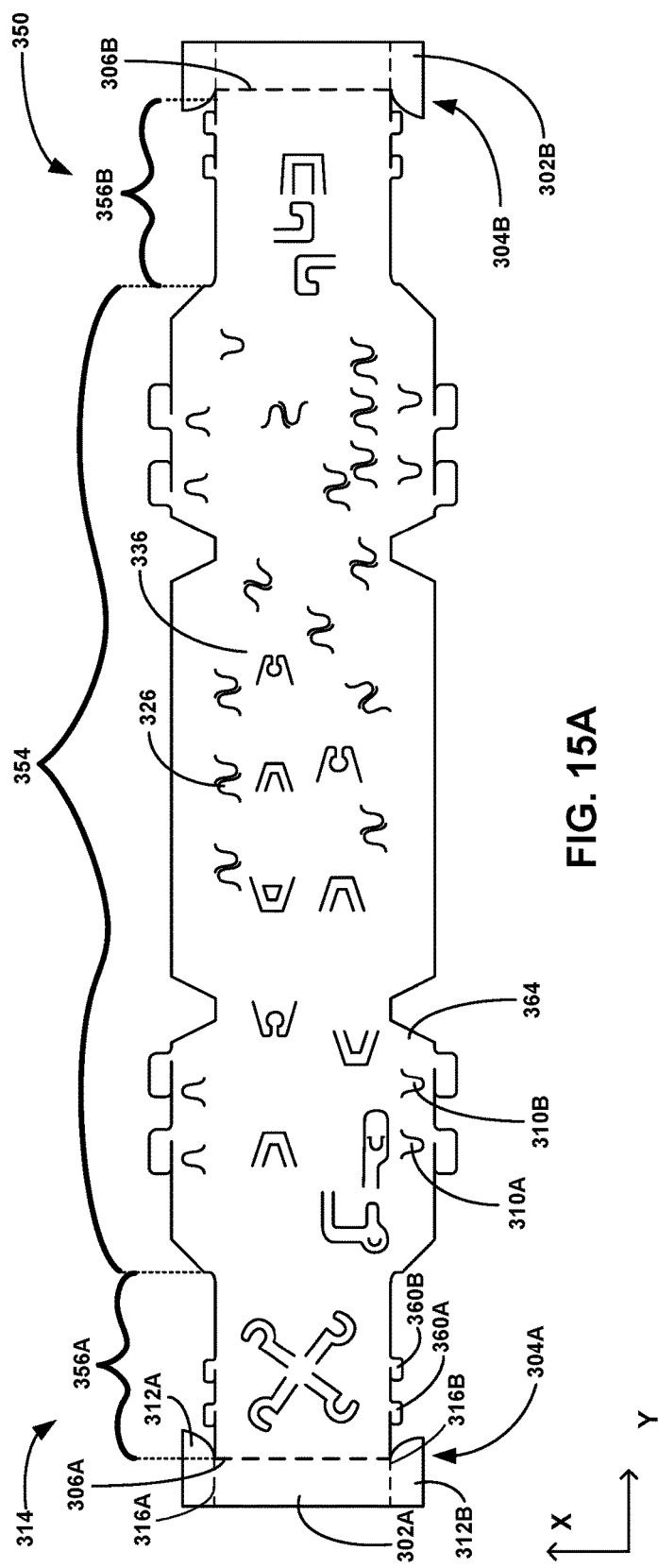
FIGS. 15A and 15B are conceptual and schematic diagrams illustrating an example backing card in a plan view and in a perspective view, respectively, as receiving a medical device.
Figure 15B:
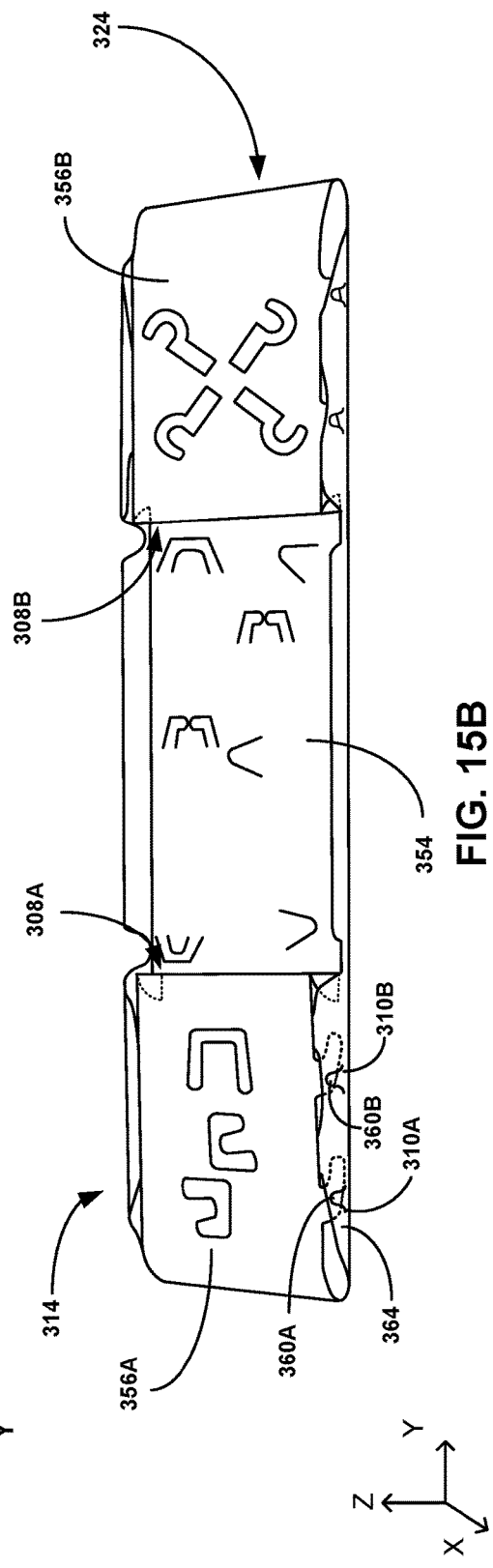

In some examples, backing cards 14 may include additional features to help secure backing card 14 in closed state 24. FIGS. 15A and 15B depict conceptual and schematic diagrams of a plan view and perspective view of another example backing card 314 in open state 350 and closed state 324, respectively. Backing card 314 may be substantially similar to backing card 14 except for any differences described herein. For example, backing card 314 may include major surface 336 that is configured to receive medical device 12 using tabs 326, where major surface 336 defines both central region 354 and flaps 356A-356B (collectively "flaps 356") that are configured to move at least partially over central region 354 to move backing card 314 to closed state 324. Major surface 336, central region 354, flaps 356, tabs 326, closed state 324, and open state 350 may be substantially similar to major surface 36, central region 54, flaps 56, tabs 26, closed state 24, and open state 50, respectively, except for any differences described herein.

Backing card 314 may include locking tabs 302A, 302B (collectively "locking tabs 302") that are located at ends 304A, 304B (collectively "ends 304") of flaps 356. A user may bend locking tabs 302 in the Z-axis direction away from flaps 356 along respective creases 306A, 306B (collectively "creases 306"). For example, locking tabs 302 may be configured to bend towards and into respective mouths 308A, 308B (collectively "mouths 308") formed by backing card 314 in closed state 324. Mouths 308 may be formed between flaps 356 and central region 354. In some examples, locking tabs 302 may further include wings 312A, 312B (collectively "wings 312"). A user may bend wings 312 along respectively creases 316A, 316B (collectively "creases 316") to be substantially perpendicular with locking tabs 302. As depicted in FIG. 15A, wings 312 may fit within side walls 364 of backing card 314 when backing card 314 is in closed state 324.

Further, backing card 314 may define side wall tabs 310, e.g., tabs 310A, 310B shown in FIG. 15A, on one or more side walls 364 of backing card 314, where side walls 364 are substantially similar to side walls 64 (FIG. 2). Side wall tabs 310 may be configured to extend away from side walls 364 in the Z-axis direction. In some of these examples, side wall tabs 310 extend away from side walls 364 along the X-Y plane after side walls 364 are moved to be around 90° with respect to major surface 336. Side wall tabs 310 may be configured to interlock with and secure flags 360A, 360B (collectively "flags 360") extending from flaps 356, where flags 360 are substantially similar to flags 60 (FIG. 2). Side wall tabs 310 may interlock with flags 360 when backing card 314 is in the closed state 324. For example, as depicted in FIG. 15B, when in closed state 324, side wall tab 310 is interlocking with flag 360A, such that a portion of flag 360 is between side wall tab 310 and side wall 364.

Figure 16:
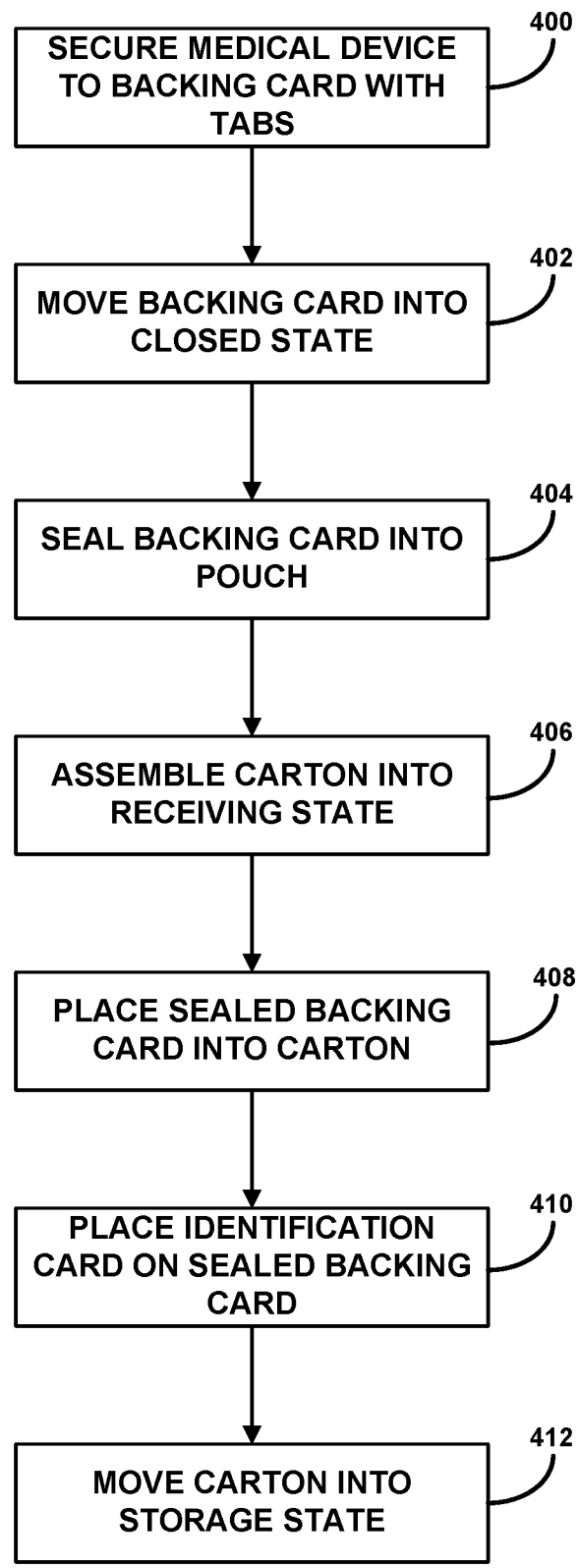
FIG. 16 is a flow diagram of an example method of securing the example medical device of FIG. 1A within the backing card, the pouch, and the carton of FIG. 1A.

FIG. 16 is a flow diagram of an example method of assembling medical device package 10. FIG. 16 is predominantly discussed using reference numerals from FIGS. 1-8, but the techniques of the example method of FIG. 16 may be executed using many different medical device packages 10 that secure many different medical devices 12. Although FIG. 16 is discussed in relation to a user executing the operations of the example method of assembling medical device package 10, in other examples a machine may execute some or all of the operations of the example method of assembling medical device package 10.

In accordance with the technique shown in FIG. 16, a user secures medical device 12 to backing card 14 (400). The user may secure medical device 12 to backing card 14 on major surface 36 of backing card 14 using tabs 26 that extend away from major surface 36. For example, the user may pull respective tabs 26 in a direction away from the major surface 36 of backing card 14 (e.g., along the Z-axis when backing card 14 is resting on an X-Y plane as described herein) and place a respective portion of medical device 12 into the elbow or hole or recess defined by tab 26 (e.g., defined as a result of pulling respective tabs 26 away from major surface 36). Once the user has placed medical device 12 within the elbow/hole/recess as defined by tabs 26, the user may "let go" of the respective tabs 26 such that tabs 26 provide a securing force upon respective portions of medical device 12. The securing force is in a direction that is generally towards major surface 36.

The user may secure medical device 12 to both central region 54 of major surface 36 and flaps 56 of major surface 36. In some examples, backing card 14 may be configured to secure specific portions of medical device 12 at specific locations of backing card 14, such that the locations at which the user secures medical device 12 to backing card 14 are predetermined. For example, medical device 12 may include a relatively bulky section (e.g., a hub or any other component that has a relatively greater cross-sectional width or diameter compared to other portions of medical device 12). In this example, backing card 14 may be configured to secure the relatively bulky portion of medical device 12 in central region 54. For example, tabs 26 of backing card 14 that are configured to secure the relatively bulky portion of medical device 12 may be at a location on central region 54 that is not covered by flaps 56 when backing card 14 is moved into closed state 24. By configuring backing card 14 to receive a relatively bulky portion of medical device 12 at a location on central region 54 which flaps 56 may not cover, backing card 14 may enable the relatively bulky portion to extend up through open space between flaps 56, rather than necessitate flaps 56 to close over the relatively bulky portion. By configuring backing card 14 to secure the relatively bulky portion at a location where the relatively bulky portion may extend through the open space, backing card 14 may reduce an overall profile of backing card 14 and therein medical device package 10.

Once the user secures medical device 12 to backing card 14, the user may move backing card 14 into closed state 24 (402). The user may move flaps 56 over at least respective portions 62 of central region 54 of backing card 14 to move backing card 14 into closed state 24. As a result of the user moving flaps 56 over at least respective portions 62 of central region 54 of backing card 14, the user may reduce a footprint of medical device package (e.g., as compared to if user placed backing card 14 within medical device package 10 when backing card 14 was in open state 50). The user may stabilize backing card 14 in closed state 24 by interlocking complementary flags 60 of backing card 14. For example, the user may stabilize backing card 14 in closed state 24 by sliding flag 60A into slot 76B between flag 60B and flap 56A (e.g., while simultaneously sliding flag 60B into slot 76A between flag 60A and side wall 64B). Once the user has stabilized backing card 14 using flags 60, the user may be handle backing card 14 in closed state 24 without backing card 14 unintentionally moving out of closed state 24.

Once the user has moved backing card 14 into closed state 24, the user may seal backing card 14 and medical device 12 in pouch 16 (404). The user may hermetically seal backing card 14 in pouch 16. In some examples, the user may sterilize pouch 16, backing card 14, and medical device 12 in a sterilization procedure as described herein, whether before or after backing card 14 and medical device 12 are sealed in pouch 16.

The user may assemble carton 20 into receiving state 22 (406). When assembling carton 20 into receiving state 22, the user may cause spacing elements 32 to define channel 34. The user may assemble carton 20 into receiving state 22 by inserting respective securing elements 104 into respective slots 122 to stabilize carton 20 in receiving state 22. Once the user has assembled carton 20 into receiving state 22, the user may place loaded pouch 38 into channel 34 of carton 20 (408). In some examples, the user may place identification card 18 on top of loaded pouch 38 (410). The user may place identification card 18 within carton 20 such that identification card 18 may prominently display information related to medical device 12 and/or medical device package 10 once carton 20 is opened (e.g., by the user or by a clinician). Further, as located within carton 20 by the user, identification card 18 may provide a further layer of protection for medical device 12.

The user may assemble carton 20 into storage state 140 (412). The user may assemble carton 20 into storage state 140 by placing spacing elements 32A, 32B over a portion of sealed backing card 14 and/or identification card 18 that is exposed within channel 34. Further, the user may assemble carton 20 into storage state 140 by folding spacing elements 32D, 32E at longitudinal ends of carton 20 at a diagonal angle back into gaps 124 adjacent ends 92 of backing card 14. The user may assemble carton 20 into storage state 140 by inserting respective securing elements 104 into respective slots 122 between exterior walls 30.

Various examples of the disclosure have been described. Any combination of the described systems, operations, or functions is contemplated. These and other examples are within the scope of the following claims.

What is claimed is:

1. A medical device package comprising:
    a backing card defining a longitudinal axis, the backing card including:
        a major surface extending lengthwise along the longitudinal axis of the backing card and including a central region and one or more flaps at one or more ends of the major surface, wherein the central region is between two longitudinal ends of the major surface; and
        a plurality of tabs configured to extend away from the major surface to secure a medical device to the major surface, wherein at least a portion of each flap is configured to move over at least a portion of the central region along the longitudinal axis to assemble the backing card into a closed state that at least partially encloses the medical device; and
    a carton configured to receive the backing card when the backing card is in the closed state, the carton including:

a set of exterior walls configured to completely enclose the backing card in the closed state when the carton is in a storage state; and a plurality of spacing elements attached to the set of exterior walls, the plurality of spacing elements being configured to receive the backing card in the closed state when the carton is in a receiving state, the plurality of spacing elements configured to secure the backing card at a position with at least a threshold distance between an outer surface of the backing card and a nearest respective portion of the set of exterior walls when the set of exterior walls encloses the backing card when the carton is in the storage state.

2. The medical device package of claim 1, wherein the set of exterior walls of the carton defines an orthotope when the carton is in the storage state.

3. The medical device package of claim 1, wherein the backing card is a first backing card, wherein at least some of the plurality of spacing elements are adjustable to secure both the first backing card and a second backing card with at least the threshold distance between an outer surface of the respective backing card and a nearest respective portion of the set of exterior walls, wherein the first backing card is a different size than the second backing card.

4. The medical device package of claim 1, wherein the backing card is physically accessible along an axis that is perpendicular to the longitudinal axis of the backing card when the plurality of spacing elements has received the backing card and the carton is in the receiving state.

5. The medical device package of claim 1, wherein the plurality of spacing elements is configured to engage the backing card along a length of the longitudinal axis of the backing card when the carton is in the storage state, such that the plurality of spacing elements applies a stabilizing force to the backing card in response to a motion of the backing card in the carton relative to the carton, where the stabilizing force is opposed to the motion.

6. The medical device package of claim 5, wherein the carton defines two gaps at longitudinal ends of the carton between a longitudinal exterior wall of the set of exterior walls and a nearest respective spacing element of the plurality of spacing elements when the backing card is received by the plurality of spacing elements and the carton is in the receiving state, wherein a top exterior wall of the set of exterior walls that is configured to close over the backing card to move the carton into the closed state is attached to spacing elements of the plurality of spacing elements that are configured to occupy the two gaps and apply at least a portion of the stabilizing force to the backing card.

7. The medical device package comprising a pouch configured to enclose the backing card, the pouch configured to create a hermetic seal around the backing card.

8. The medical device package comprising a tray defining a recess configured to receive the backing card, the tray including a layer configured to hermetically seal the recess when the recess receives the backing card.

9. A medical device package comprising:
a medical device;
a backing card defining a longitudinal axis, the backing card including:
a major surface configured to receive the medical device when the backing card is in an open state, the major surface extending lengthwise along the longitudinal axis of the backing card and including a central region and one or more flaps on one or more ends of the major surface along the longitudinal axis;
a plurality of tabs configured to extend away from the major surface to secure the medical device to the major surface, wherein at least a portion of each of the one or more flaps is configured to move over at least a portion of the central region along the longitudinal axis to assemble the backing card into a closed state that at least partially encloses the secured medical device;
a pouch configured to enclose the backing card, the pouch configured to create a hermetic seal around the backing card; and
a carton configured to receive the backing card when the backing card is in the closed state, the carton including:
a set of exterior walls configured to completely enclose the backing card in the closed state; and
a plurality of spacing elements attached to the set of exterior walls, the spacing elements being configured to secure the backing card at a position with at least a threshold distance between an outer surface of the backing card and the nearest respective portion of the set of exterior walls when the set of exterior walls enclose the backing card.

10. The medical device package of claim 9, wherein the carton defines empty space between a longitudinal end of the backing card in the closed state and a longitudinal end of the carton, further comprising a support box that is configured to occupy the empty space and provide a stabilizing force on both the longitudinal end of the backing card and the longitudinal end of the carton.

11. The medical device package of claim 9, wherein the backing card further includes one or more handles that extend longitudinally from one or more longitudinal ends of the backing card when the backing card is in the open state.

12. A method comprising:
securing a medical device to a major surface of a backing card using a plurality of tabs of the backing card when the backing card is in an open state, the major surface including a central region and one or more flaps at one or more ends of the major surface, wherein the central region is between two longitudinal ends of the major surface;
moving the backing card from the open state to the closed state by moving at least a portion of each flap over at least a portion of the central region such that the one or more flaps at least partially enclose the secured medical device, and
loading the backing card into a channel of a carton that includes a set of exterior walls and a plurality of spacing elements attached to the set of exterior walls, the plurality of spacing elements defining the channel at a position with at least a threshold distance between an outer surface of the backing card and the nearest respective portion of the set of exterior walls.

13. The method of claim 12, further comprising moving the carton into a storage state in which the set of exterior walls completely enclose the backing card as received in the channel.

14. The method of claim 12, further comprising adjusting one or more spacing elements of the carton to modify the threshold distance.

* * * * *